(12) United States Patent
Grim et al.

(10) Patent No.: US 11,399,952 B2
(45) Date of Patent: Aug. 2, 2022

(54) MEDICAL IMPLANT HAVING AN ANCHORING SYSTEM AND METHOD OF USE THEREOF

(71) Applicant: Alliance Partners LLC, San Antonio, TX (US)

(72) Inventors: Gregory Andrew Grim, San Antonio, TX (US); Karl W. Swann, San Antonio, TX (US)

(73) Assignee: Alliance Partners LLC, San Antonio, TX (US)

( * ) Notice: Subject to any disclaimer, the term of this patent is extended or adjusted under 35 U.S.C. 154(b) by 0 days.

(21) Appl. No.: 17/183,092

(22) Filed: Feb. 23, 2021

(65) Prior Publication Data

US 2021/0169659 A1  Jun. 10, 2021

Related U.S. Application Data

(63) Continuation of application No. 16/258,054, filed on Jan. 25, 2019, now Pat. No. 10,925,748.

(60) Provisional application No. 62/621,663, filed on Jan. 25, 2018, provisional application No. 62/621,671, filed on Jan. 25, 2018.

(51) Int. Cl.
*A61F 2/44* (2006.01)
*A61F 2/30* (2006.01)
*A61F 2/46* (2006.01)

(52) U.S. Cl.
CPC ............ *A61F 2/4425* (2013.01); *A61F 2/442* (2013.01); *A61F 2/446* (2013.01); *A61F 2/447* (2013.01); *A61F 2/4455* (2013.01); *A61F 2/4637* (2013.01); *A61F 2002/30477* (2013.01); *A61F 2002/30579* (2013.01)

(58) Field of Classification Search
CPC .......... A61F 2/44; A61F 2/442; A61F 2/4425; A61F 2002/443; A61F 2/4455; A61F 2/446; A61F 2/447; A61F 2002/30579
See application file for complete search history.

(56) References Cited

U.S. PATENT DOCUMENTS 8,080,062 B2 * 12/2011 Armstrong ............ A61F 2/4465
623/17.11

* cited by examiner

*Primary Examiner* — Larry E Waggle, Jr.
(74) *Attorney, Agent, or Firm* — Dickinson Wright PLLC; Ross Spencer Garsson

(57) ABSTRACT

An improved cage that has an anchoring system and method of use thereof. The anchoring system has movable/expandable jaw portions that can expand vertically (i.e., upward and downward relative to the respective superior and inferior surfaces of the cage) so that the cage can be more securely implanted in position. The superior and inferior expandable portions of the anchoring system move vertically by the rotation of one or more spindles that is incorporated in the jaw mechanism (and/or by the rotation of a lead screw that is incorporated in the cage). In some embodiments, the medical implant (such as a cage) is itself non-expandable (i.e., the height of the medical implant does not change). In other embodiments, the medical implant (such as a cage) can be expanded independently of the anchoring system.

20 Claims, 30 Drawing Sheets

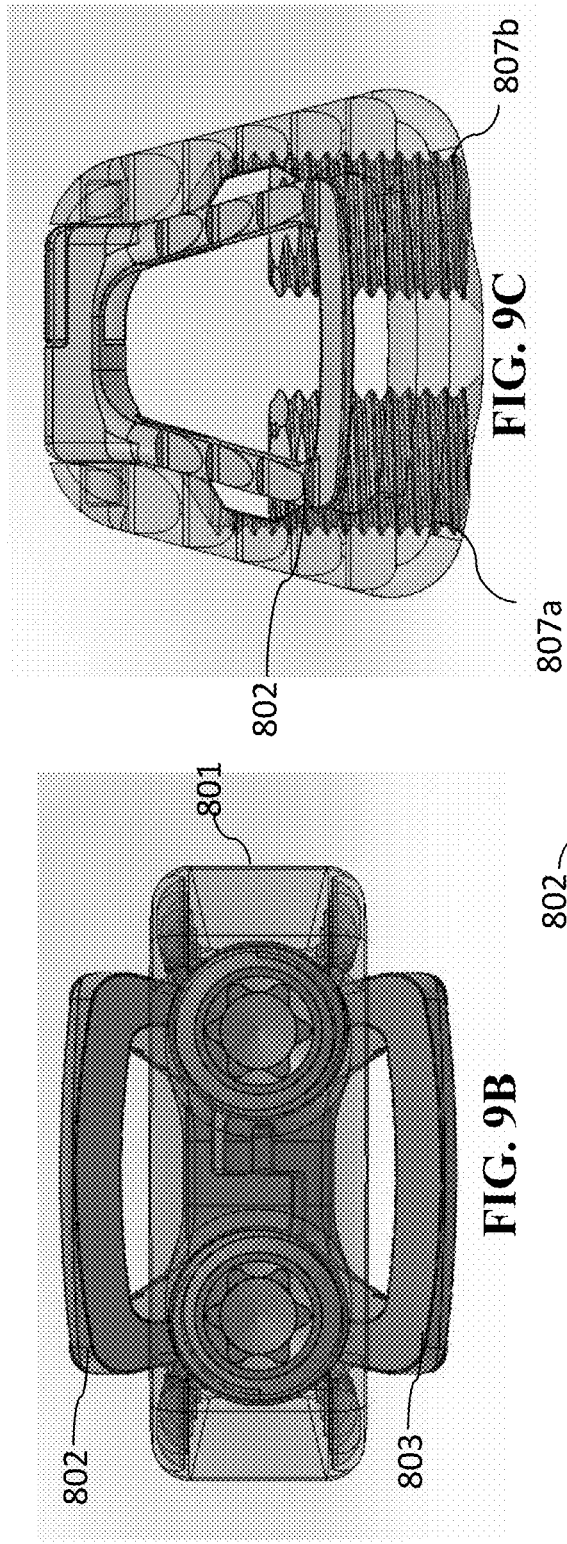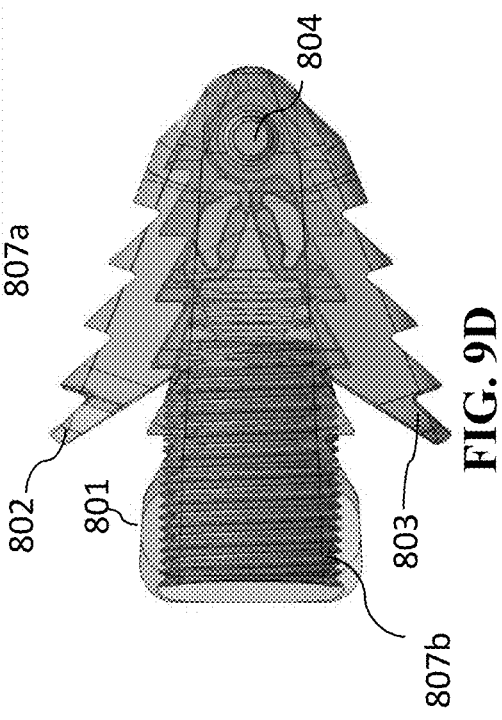

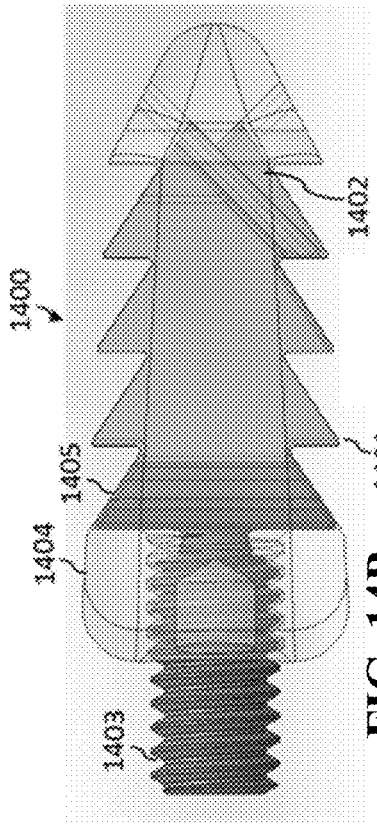
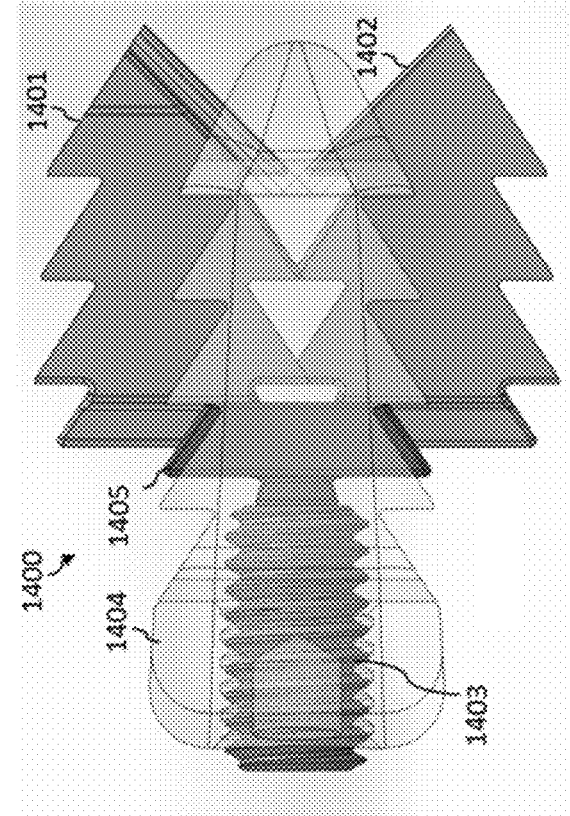
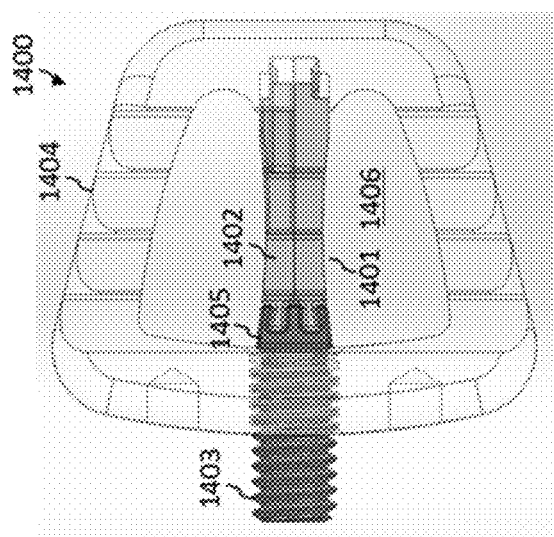
FIG. 14B
FIG. 14C
FIG. 14A

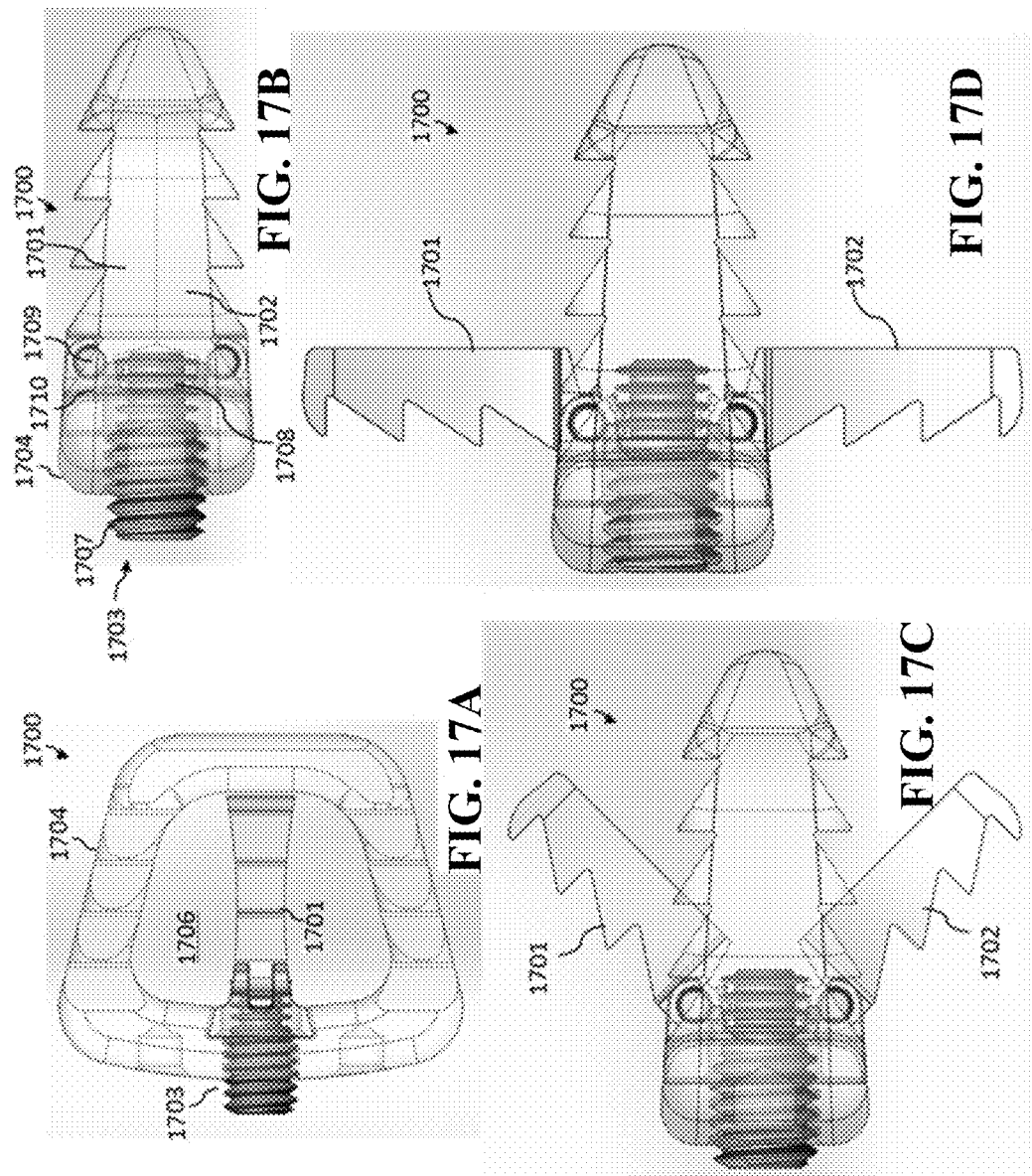

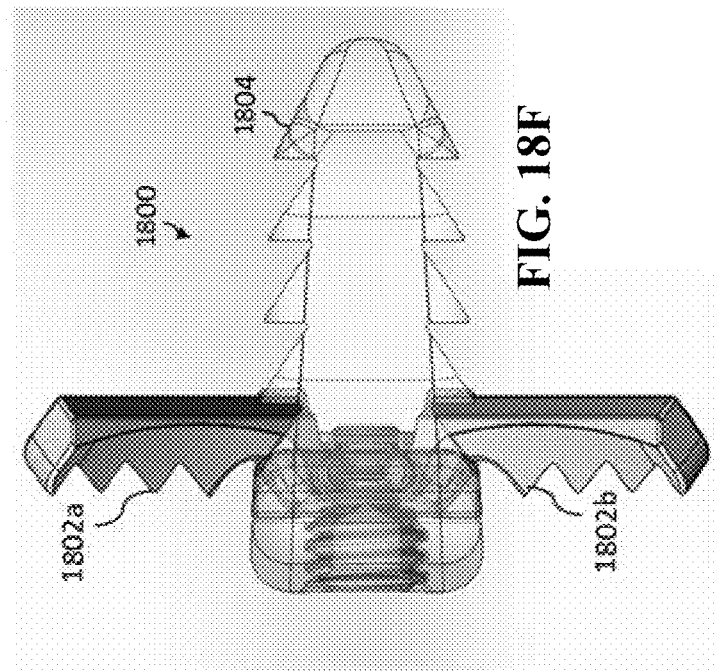
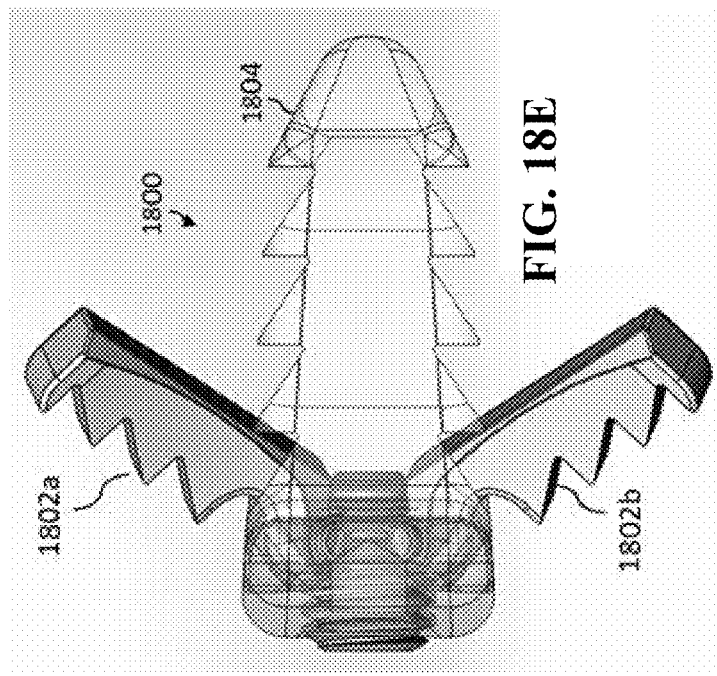

MEDICAL IMPLANT HAVING AN ANCHORING SYSTEM AND METHOD OF USE THEREOF

CROSS-REFERENCE TO RELATED APPLICATIONS

This application is a continuation of U.S. patent application Ser. No. 16/258,054, filed Jan. 25, 2019, entitled "Medical Implant Having An Anchoring System And Method Of Use Thereof, which claims priority benefits to U.S. Provisional Patent Application Serial No. 62/621,663, and 62/621,671, each filed on Jan. 25, 2018, and each entitled "Medical Implant Having An Anchoring System And Method Of Use Thereof," which patent applications are commonly assigned to the Assignee of the present invention and are hereby incorporated herein by reference in their entirety for all purposes.

FIELD OF INVENTION

A medical implant having an anchoring system for anchoring and retaining the medical implant (such as a cage) in place and method of use thereof.

BACKGROUND OF INVENTION

The spine is the axis of the skeleton on which all of the body parts hang. In humans, the normal spine has seven cervical segments, twelve thoracic segments, five lumbar segments, five sacral segments (which fuse to form the sacrum) and three to five coccygeal segments (which fuse to form the coccyx. The lumbar spine attaches to the pelvis, and in turn is supported by the hip and leg bones. The bony vertebral bodies of the spine are separated by intervertebral discs, which act as joints but allow known degrees of flexion, extension, lateral bending, and axial rotation and translation.

Typical vertebra has a thick anterior bone mass called the vertebral body, with a neural (vertebral) arch that arises from the posterior surface of the vertebral body. The centers of adjacent vertebrae are supported by intervertebral discs. The disc and/or vertebral bodies may be displaced or damaged due to trauma, disease, degenerative defects, or aging over an extended period of time. One result of this displacement or damage to an intervertebral disc or vertebral body may be chronic back pain. In many cases, to alleviate back pain from degenerated or herniated discs, part or all of the disc is removed and may be replaced with an implant that promotes fusion of the remaining bony anatomy.

The success or failure of spinal fusion may depend upon several factors. For instance, the spacer or implant or cage used to fill the space left by the removed disc must be sufficiently strong to support the spine under a wide range of loading conditions. The spacer should also be configured so that it is likely to remain in place once it has been positioned in the spine by the surgeon. Additionally the material used for the spacer should be biocompatible material and should have a configuration that promotes bony ingrowth.

Other types of medical implants, such as corpectomy cages, have also been developed to help support the spine and maintain the normal spacing between opposing vertebrae. Typically, corpectomy cages are pre-manufactured at various heights requiring that a cavity between opposing vertebrae be prepared and distracted to a dimension corresponding to the most suitably sized corpectomy cage. The surgical procedure to prepare the implant site can be difficult and lengthy. Moreover, the procedure can increase risk of trauma to the tissues surrounding of the implant site.

Distractible corpectomy cages may be used as both a fusion device and/or a means for maintaining intervertebral spacing. Sometimes these implants include an actuation mechanism that allows the corpectomy cage to be expanded in situ to a size that corresponds to the cavity created when the damaged tissue is removed. These medical implants are referred to as "expandable medical implants" or "expandable cages." The activation mechanism typically includes devices such as gears, threaded rods, and the like, in mechanical engagement so as to expand or contract the device to a necessary distance between the vertebrae. For medical implants that have cages that do not expand in situ, these are referred to as "non-expandable medical implants" or "non-expandable cages."

Cervical cages are also used to stabilize the spine during the fusion process. An example of a cervical cage is the Alamo® Cervical Intervertebral Body Fusion device (Alliance Spine, San Antonio, Tex.), which is shown in FIG. 1. In FIG. 1, cage 100 is shown inserted in spinal column 101. Such cage 100 can be manufactured from PEEK Optima® LT1 (Invibio Biomaterial Solutions, West Conshohocken, Pa.) per ASTM F2026 and includes tantalum markers per ASTM F560 for radiographic visualization.

Furthermore, the cage can have the following features and benefits:

Length and width footprint can vary, such as 12 mm×14 mm, 14 mm×17 mm, and 16 mm×20 mm.

Heights can often vary in 1 mm increments from 5 mm to 12 mm (although these heights can be outside these ranges depending upon the patient).

The cage can have teeth on superior and inferior surfaces, which are designed to provide secure engagement and to prevent expulsion and migration.

The cage can be made of a biocompatible radiolucent polymer, which allows clear assessment of bony fusion. Alternatively, the cage can be made with a titanium alloy or a combination of a biocompatible radiolucent polymer and titanium alloy.

The cage can have a large graft area, which allows for optimal bone graft placement.

A top view of an exemplar intervertebral/interbody cage (cage 200) is shown in FIG. 2. For orientation purposes terms like "anterior," "posterior," "sagittal," "superior," and "inferior" are describing front, back, side, top, and bottom, respectively for the normal orientation of use of a medical implant, such as cage 200. As shown in FIG. 2, cage has anterior end 202, posterior end 201, lateral sides 203 and 204, superior face (which is the top view shown for cage 200 in FIG. 2), and inferior face (which is not shown in FIG. 2 as it is the underside of cage 200 as illustrate in this FIG. 2).

The "lateral" sides are positioned in a direction that is parallel to the plane of the sagittal view, i.e., the lateral sides are in a parasagittal plane. When lateral sides move outward ("lateral") or inward ("medial") relative to one another, these lateral sides are referred to as moving in a "lateral direction" or "medial direction," respectively, in the normal orientation of use of an anterior medical implant of the present invention.

The "vertical" direction is the direction in the plane of the superior/inferior views, i.e., when the superior and inferior faces move upward/downward relative to one another, these superior and inferior faces are referred to as moving in a vertical direction. It should be noted that due to symmetry of many medical implants, the "superior" and "inferior" sides are interchangeable (in that the medical device can be flipped). Thus, the superior and inferior sides are relative to one another. The height of a medical implant is measured in the vertical direction. Moreover, when the medical implant has an expandable height, the expanding is done in the vertical direction.

As shown in FIG. 2, the cage does not expand either vertically or laterally, and therefore is a non-expandable cage.

U.S. Pat. No. 8,328,872 issued Dec. 11, 2012 to Duffield et al. ("Duffield") discloses an intervertebral implant for implantation in a treated area of an intervertebral space between vertebral bodies of a spine, which includes a cage having screw holes extending from a side portion to the inferior (bottom) and superior surfaces (top) of the cage, in which the cage portion contains screws holes for receiving screws. There is also a screw back out prevention mechanism adapted on the plate portion and prevents the back out of screws from the screw holes. Illustration of the Duffield cage is shown in FIGS. 3A-3C. FIG. 3A is a perspective view of the cage 300. FIG. 3B is a sagittal view of cage 300. FIG. 3C is a perspective view of cage 300 with fasteners (screws 301) inserted. Other than changes in the reference numbers, FIGS. 3A-3C correspond to FIGS. 1, 3, and 7, respectively of Duffield. The screw holes of cage 300 are situated for receiving bone screws 301 that can be attached to the adjacent vertebral bodies at different angles to secure the cage in its position.

As the medical implant (cage) is subject to movement when the surgeon/practitioner is inserting and securing it, there is a need for an improved anchoring system that allows a surgeon to more consistently and conveniently hold secure and anchor the medical implant in place.

SUMMARY OF INVENTION

The present invention regards an improved cage that has an anchoring system. The anchoring system has movable/expandable jaw portions that can expand vertically (i.e., upward and downward relative to the respective superior and inferior surfaces of the cage) so that the cage can be more securely implanted in position. The superior and inferior expandable portions of the anchoring system move vertically by the rotation of one or more spindles that is incorporated in the jaw mechanism. In some embodiments, the medical implant (such as a cage) is itself non-expandable (i.e., the height of the medical implant does not change). In other embodiments, the medical implant (such as a cage) can be expanded independently of the anchoring system.

In general, in one aspect, the invention features a medical implant. The medical implant includes a medical implant body having a superior surface and an inferior surface. The superior surface and the inferior surface are on opposing sides of the medical implant body. The medical implant further includes an anchoring mechanism attached to the medical implant body. The anchoring mechanism includes a superior anchoring section having an anterior portion of the superior anchoring section and a posterior portion of the superior anchoring section. The anchoring mechanism further includes an inferior anchoring section having an anterior portion of the inferior anchoring section and a posterior portion of the inferior anchoring section. The posterior portion of the superior anchoring section is pivotably connected to the posterior portion of the inferior anchoring section at a pivot joint. The superior anchoring portion and inferior anchoring portion are operable to pivot about the pivot joint such that the anterior portion of the superior anchoring portion and the anterior portion of the inferior anchoring portion pivot away from one another. The anchoring mechanism further includes at least one spindle or lead screw that is operable to move between a first position and at least one second position. When the at least one spindle or lead screw is in the first position, the anchoring mechanism is in the closed position with the anterior portion of the superior anchoring section in close proximity to the anterior portion of the inferior anchoring section. When the at least one spindle or lead screw is in the second position the anchoring mechanism has moved to a first opened position. In the first opened positon, the anterior portion of the superior anchoring section and the anterior portion of the inferior anchoring portion are pivoted away from one another about the pivot joint. The at last one spindle or lead screw is operable to be maintained at the second position to lock the anchoring mechanism in the opened position.

In general, in another aspect, the invention features a method. The method includes positioning a medical implant between a first vertebrae and a second vertebrae of a spinal column. The first vertebrae and the second vertebrae are adjacent. The medical implant includes a medical implant body and an anchoring system. The anchoring system includes a superior anchoring section having an anterior portion of the superior anchoring section and a posterior portion of the superior anchoring section. The anchoring system further includes an inferior anchoring section having an anterior portion of the inferior anchoring section and a posterior portion of the inferior anchoring section. The posterior portion of the superior anchoring section is pivotably connected to the posterior portion of the inferior anchoring section at a pivot joint such that the anterior portion of the superior anchoring section and the anterior portion of the inferior anchoring section can move pivotably away from one another. The anchoring mechanism is in a closed position in which the anterior portion of the superior anchoring section in close proximity to the anterior portion of the inferior anchoring section. At least one spindle or lead screw that is operable to move the anchoring mechanism from the closed position to at least one opened position. The method further includes coupling a rotating tool to at least one of the at least one spindle or lead screw. The method further includes using the rotating tool to rotate the spindle or lead screw to move the anchoring mechanism from the closed position to one of the at least one opened position. The rotation of the spindle or lead screw causes the anterior portion of the superior anchoring section to move in a direction toward the first vertebrae and causes the anterior portion of the inferior anchoring section to move in a direction toward the second vertebrae such that the anterior portion of the superior anchoring section and the anterior portion of the inferior anchoring section anchor the cage implant between the first vertebrae and the second vertebrae. The method further includes removing the rotating tool from the spindle or lead screw.

Implementations of the invention can include one or more of the following features:

The at least one spindle or lead screw can be at least one spindle.

The medical implant body can include at least one superior recess located at an anterior superior portion of the medical implant body and at least one inferior recess located at an anterior inferior portion of the medical implant body. The anchoring mechanism can further include a compressor operatively connected to the superior anchoring section and the inferior anchoring section that provides a compressive force to compress the anchoring mechanism in the closed position. Each of the at least one spindle can have a separator. The spindle can be located between the anterior portion of the superior anchoring section and the anterior portion of the inferior anchoring section and at the anterior portion of the medical implant. The spindle can be rotatable so that the separator is operable to move between a first spindle position and a second spindle position. When the separator is in the first spindle position, the anchoring mechanism can be in the closed position. When the separator is in the second spindle position, the anchoring mechanism can be in the first opened position. When the separator is in the second position, the separator can be in contact with at least one of the at least one superior recess and at least one of the at least one inferior recess, which are operable to maintain the separator in the second separator position which maintains the spindle in the second position.

The anchoring mechanism can be a single-opened-height controlled anchoring system.

The anchoring mechanism can be a multiple-opened-height controlled anchoring system.

The medical implant body can include at least one additional superior recess located at the anterior superior portion of the medical implant body and at least one additional inferior recess located at the anterior inferior portion of the medical implant body. The medical implant can include a locking ring operable to lock the spindle. The spindle can be rotatable so that the separator is operable to move between the first spindle position and a third spindle position. When the separator is in the third spindle position, the anchoring mechanism can be in a second opened position that is different than the first opened position. When the separator is in the third spindle position, the separator can be in contact with at least one of the at least one additional superior recess and at least one of the at least one additional inferior recess. The locking ring can be operable to lock the spindle from rotating.

The anchoring mechanism can include at least two spindles.

The at least one spindle or lead screw can be at least one lead screw, and the anchoring mechanism can be a variable-opened-height controlled anchoring system The at least one lead screw can be operable to move to at least a third position. When the at least one lead screw is in the third position, the anchoring mechanism can be in a second opened position in which the anterior portion of the superior anchoring section and the anterior portion of the inferior anchoring portion are pivoted away from one another about the pivot joint even farther than when the lead screw was in the second position.

When the at least one lead screw is in the third position, the anchoring mechanism can be in a fully opened position.

The at least one lead screw can be operable to move to at least a fourth position. When the at least one lead screw is in the fourth position, the anchoring mechanism can be in a third opened position. In the third opened position, the anchoring mechanism can be more opened than when in the first opened position and less opened when in the second opened position.

The medical implant can be a cage.

The cage can be a lumbar cage.

The lumbar cage can include at least two of the spindles or at least two of the lead screws.

The lumbar cage can be a thoraco-lumbar cage.

The lumbar cage can have a length and a width selected from a group consisting of 22 mm×30 mm, 24 mm×32 mm, 28 mm×36 mm, and 32 mm×40 mm.

The cage can be a cervical cage.

The cervical cage can include exactly one spindle or exactly one lead screw.

The cervical cage can have a length and a width selected from a group consisting of 12 mm×14 mm, 14 mm×17 mm, and 16 mm×20 mm.

The medical implant can have a height between 5 mm and 22 mm.

The medical implant can be a vertebral body replacement having a height between 20 mm and 100 mm.

The medical implant can include a material selected from a group consisting of biocompatible radiolucent polymers, non-radiolucent metal alloys, carbon fibers, composites of carbon fibers and polymers, and combinations thereof.

The anchoring mechanism can include a material selected from a group consisting of metal alloys, ceramics, polymers, and composites thereof.

The anchoring mechanism can include a metal alloy or a carbon composite.

The metal alloy can include a titanium metal alloy.

The medical implant body can be a non-expandable medical implant body.

The medical implant body can be an expandable medical implant body.

The anchoring mechanism can be operable to anchor the medical implant before expanding the expandable medical implant body.

The expandable medical implant body can expand in a vertical direction to expand the height of the medical implant body. The maximum expanded height of the expandable medical implant body can be less than the difference between the anterior portion of the superior anchoring section and the anterior portion of the inferior anchoring section when the anchoring mechanism is in the first opened position.

The medical implant can further include a plurality of fastener window features through which a fastener can pass through for anchoring of the medical implant.

The plurality of fastener window features can be operable for receiving a fastener selected from a group consisting of (a) fixed angle screws, (b) variable angle screws, (c) self-drilling screws, (d) self-tapping screws, and (e) combinations thereof.

The present invention further regards an improved cage that has movable/expandable anchoring portions that can expand vertically upward and downward (relative to the respective superior and inferior surfaces of the cage) so that the cage can be more securely implanted (i.e., anchored) in position. The superior and inferior expandable portions are readily expandable (vertically upwards and downwards) by the rotation of a lead screw that is incorporated in the cage. In some embodiments, the medical implant (such as a cage) is itself non-expandable (i.e., the height of the medical implant body does not change). In other embodiments, the medical implant body (such as a cage) can also be expanded independently of the anchoring system.

In general, in one aspect, the invention features a medical implant. The medical implant includes a medical implant body having a superior surface and an inferior surface. The superior surface and the inferior surface are on opposing sides of the medical implant body. The medical implant further includes an anchoring mechanism that includes a first expandable section, a second expandable section, and a lead screw. The anchoring mechanism is operable to expand a portion of the first expandable section in a first direction such that the portion of the first expandable section is outside of the superior surface of the medical implant body. The first direction is vertically upward relative to the superior surface.

The anchoring mechanism is further operable to expand a portion of the second expandable section in a second direction such that the portion of the second expandable section is outside the inferior surface of the medical implant body. The second direction is vertically downward relative to the inferior surface. The lead screw is rotatably connected to the medical implant body and operable to rotate between a first position and a second position. When the lead screw is in the first position, the anchoring mechanism is in a closed position in which the portion of the first expandable section is within the medical implant body and the portion of the second expandable section is within the medical implant body. When the lead screw is in the second position, the anchoring mechanism is in a second position in which the portion of the first expandable section is outside the superior surface of the medical implant body and the portion of the second expandable section is outside the inferior surface of the medical implant body. The lead screw is further operable to be locked in place (and not rotate) to maintain the portion of the first expandable section and the portion of the second expandable section in place.

In general, in another aspect, the invention features a method. The method includes positioning a medical implant between a first vertebrae and a second vertebrae of a spinal column. The first vertebrae and the second vertebrae are adjacent. The medical implant includes a medical implant body having a superior surface and an inferior surface. The superior surface and the inferior surface are on opposing sides of the medical implant body. The medical implant further includes an anchoring mechanism that includes a first expandable section, a second expandable section, and a lead screw. The anchoring mechanism is operable to expand a portion of the first expandable section in a first direction such that the portion of the first expandable section is outside of the superior surface of the medical implant body. The first direction is vertically upward relative to the superior surface. The anchoring mechanism is further operable to expand a portion of the second expandable section in a second direction such that the portion of the second expandable section is outside the inferior surface of the medical implant body. The second direction is vertically downward relative to the inferior surface. The lead screw is rotatably connected to the medical implant body and operable to rotate between a first position and a second position. When the lead screw is in the first position, the anchoring mechanism is in a closed position in which the portion of the first expandable section is within the medical implant body and the portion of the second expandable section is within the medical implant body. When the lead screw is in the second position, the anchoring mechanism is in a second position in which the portion of the first expandable section is outside the superior surface of the medical implant body and the portion of the second expandable section is outside the inferior surface of the medical implant body. The lead screw is further operable to be locked in place (and not rotate) to maintain the portion of the first expandable section and the portion of the second expandable section in place. The method further includes coupling a rotating tool to the lead screw. The method further includes using the rotating tool to rotate the lead screw to move the anchoring mechanism from the closed position to the opened position. The rotation of the lead screw causes the portion of the first expandable section to move in a direction toward the first vertebrae and causes the portion of the second expandable section to move in a direction toward the second vertebrae such that the anchoring mechanism anchors the medical implant between the first vertebrae and the second vertebrae. The method further includes removing the rotating tool from the lead screw.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

It is also to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

For a more complete understanding of the present invention, and the advantages thereof, reference is now made to the following descriptions taken in conjunction with the accompanying drawings, in which:

FIG. 3A shows a perspective view. FIG. 3B shows a sagittal view. FIG. 3C shows a perspective view with fasteners.

FIGS. 9A-9D depict different views of the alternative cervical cage embodiment of the present invention shown in FIGS. 8A-8D in which the variable-opened-height controlled anchoring system is shown in an opened (or anchored) position (in which the variable-opened-height controlled anchoring system is only partially opened).

FIGS. 14A-14C depict different views of another embodiment of the present invention.

FIGS. 17A-17D depict different views of another embodiment of the present invention.

FIGS. 18A-18H depict different views of another embodiment of the present invention.

DETAILED DESCRIPTION

The medical implant having an anchoring system for anchoring and retaining the medical implant (such as a cage) in place and method of use thereof. The medical implant can be placed between the vertebrae and then utilizing a tool to rotate the anchoring system from the closed position to the opened (or partially opened) position, to secure and anchor the medical implant in place. In some embodiments, the partially opened positions is controllable (i.e., the degree by which the anchoring system is opened is variable and/or can be controlled in variable states. This anchoring can be done without having to insert any screws or other fasteners. Optionally, after the anchoring system is in place, more traditional fasteners (such as screws) can then be utilized for further securing of the medical implant. Such optional anchoring is done more likely in lumbar cage embodiments (as compared to cervical cage embodiments).

The medical implant fixation instrument can also afford the surgeon with graft windows so that the bone growth inducing substance can still utilized with the medical implant or so that fusion can be more readily viewed by the surgeon/practitioner.

While the figures refer to medical implant fixation system to be used for an anterior placement orientation, the medical implant fixation system can be used in orientation and with a variety of medical implant systems (such as with plates).

Cage Embodiments with Single-Opened-Height Controlled Anchoring Systems

Referring to the figures, a first embodiment of the present invention is depicted in FIGS. 4A-4C and FIGS. 5A-5C, which is a cage embodiment that has a single-opened position. "Single-opened position" refers to that the cage embodiment has only one vertical height of the anchoring system when in the opened position, i.e., the vertical height cannot be varied by the surgeon/practitioner once the particular cage has been selected (except of course, for the change in vertical height caused by moving the anchoring system between the closed and open positions). Such cage embodiments are referred to herein as cage embodiments having "single-opened-height controlled anchoring systems." Hence, the surgeon/practitioner must determine the expected vertical opened-height of the anchoring system when selecting which cage embodiment to use. As discussed below, some cage embodiments have variable opened-heights in that the anchoring system can be partially opened to various degrees, including completely opened. Such cage embodiments are referred to herein as cage embodiments having "variable-opened-height controlled anchoring systems." Such variable-opened-height controlled anchoring systems provide the surgeon/practitioner the ability to vary the vertical height when anchoring those cage embodiments.

Figure 4A:
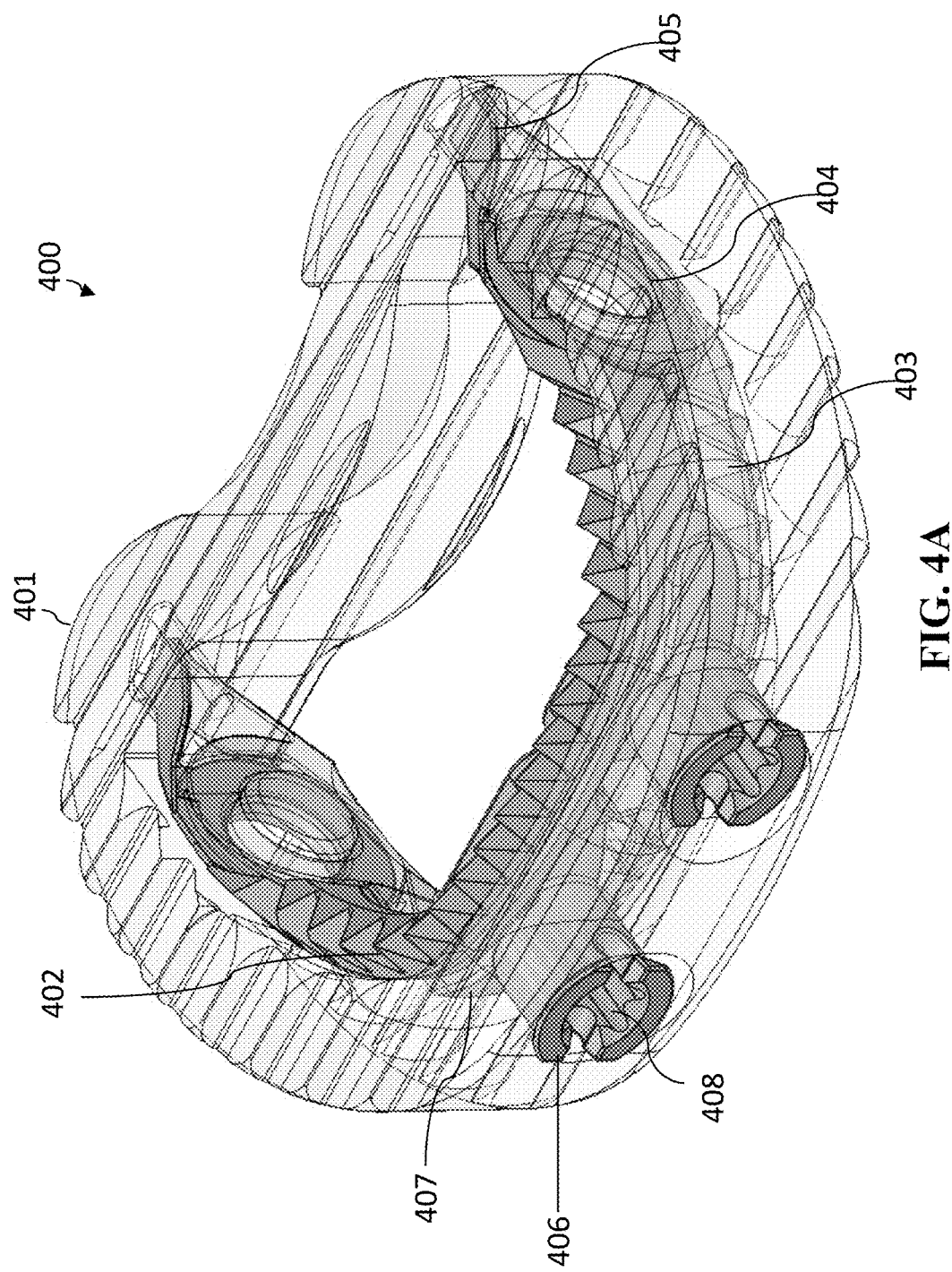
FIG. 4A-4C depict different views of a lumbar cage embodiment of the present invention in which the anchoring system is a single-opened-height controlled anchoring system shown in the closed (or unanchored) position.
Figure 4B:
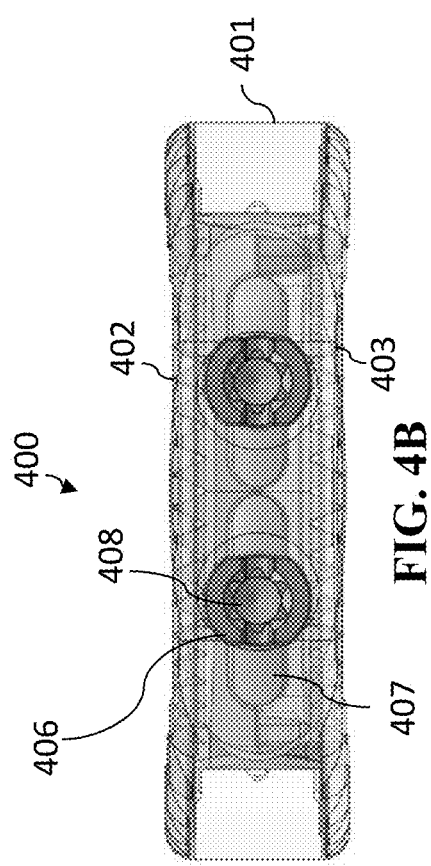
Figure 4C:
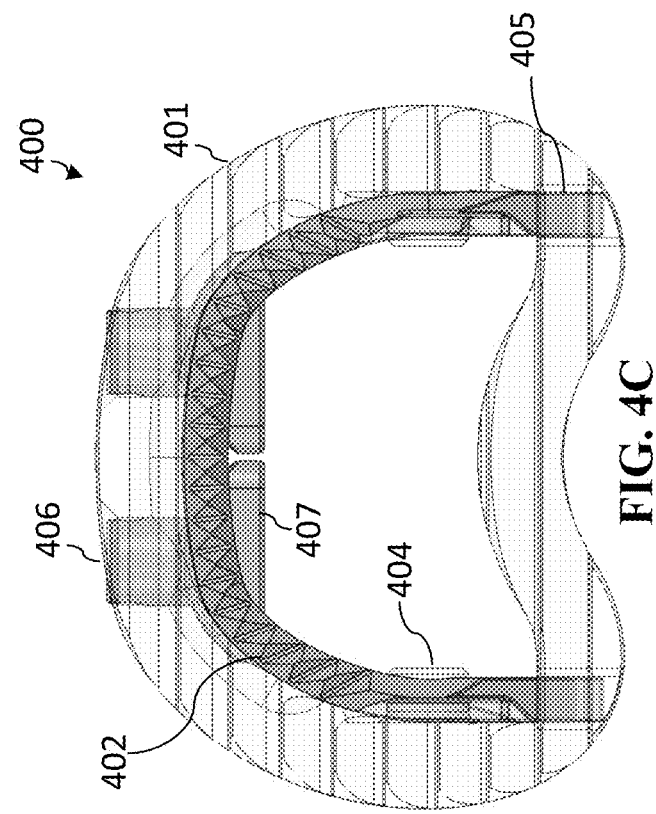

FIGS. 4A-4C show cage 400 with the anchoring portions (superior anchoring portion 402 and inferior anchoring portion 403) in a closed position. FIGS. 4A-4C are, respectively, perspective, anterior, and superior view of cage 400.

As shown in FIGS. 4A-4C, the cage 400 has a cage body 401 which is of standard materials and size of typical intervertebral/interbody cage. The cage 401 can be made of a polymer, such as PEEK Optima® LT1 or a titanium alloy (such as per ASTM F136). Connected to the cage body 401 is an anchoring mechanism (such as a jaw mechanism) that includes (a) a superior anchoring section 402 (superior jaw section) and an inferior anchoring section 403 (inferior jaw section). The anchoring sections can be made of a polymer, a metal (such as a titanium alloy), or a combination thereof.

In the closed position (such as shown in FIGS. 4A-4C), the superior anchoring section 402 and inferior anchoring section 403 are in close proximity, typically in contact, with one another. The superior anchoring section 402 and inferior anchoring section 403 are pivotably connected to one another at pivot joint 404. The pivot joint 404 is located toward the posterior section of the cage 400 such that when the superior anchoring section 402 and inferior anchoring section 403 pivot about pivot joint 404, they will separate farther apart at the anterior section of cage 400. On the other side of the pivot joint 404 (closer to the posterior section of cage 400), the superior anchoring section 402 and inferior anchoring section 403 have end portions 405. Generally, the superior anchoring section 402 and inferior anchoring section 403 are spring loaded (such as by end portions 405) or have some other compression mechanism so that the forces are compressing superior anchoring section 402 and inferior anchoring section 403 toward one another. I.e., absent other forces, the superior anchoring section 402 and inferior anchoring section 403 will tend toward contacting one another, such that the anchoring system in cage 400 will be in the closed position, as depicted in FIGS. 4A-4C.

Cage 400 further includes a spindle 406 that is rotatable. Spindle 406 also has a central feature 408 that is operable to accept a rotational tool, so that spindle 406 can be rotated. As shown in FIGS. 4A-4C, spindle 406 is located at the anterior of cage 400 and is located between the anterior portions of superior anchoring section 402 and inferior anchoring section 403. Spindle 406 includes a separator 407 that is in contact with the superior anchoring section 402 and inferior anchoring section 403.

Again, FIGS. 4A-4C show the anchoring mechanism in the closed position, accordingly, the separator 407 of the spindle 406 is positioned in a direction that provides for the superior anchoring section 402 and inferior anchoring section 403 to be in close proximity (typically in contact) with one another.

Figure 5A:
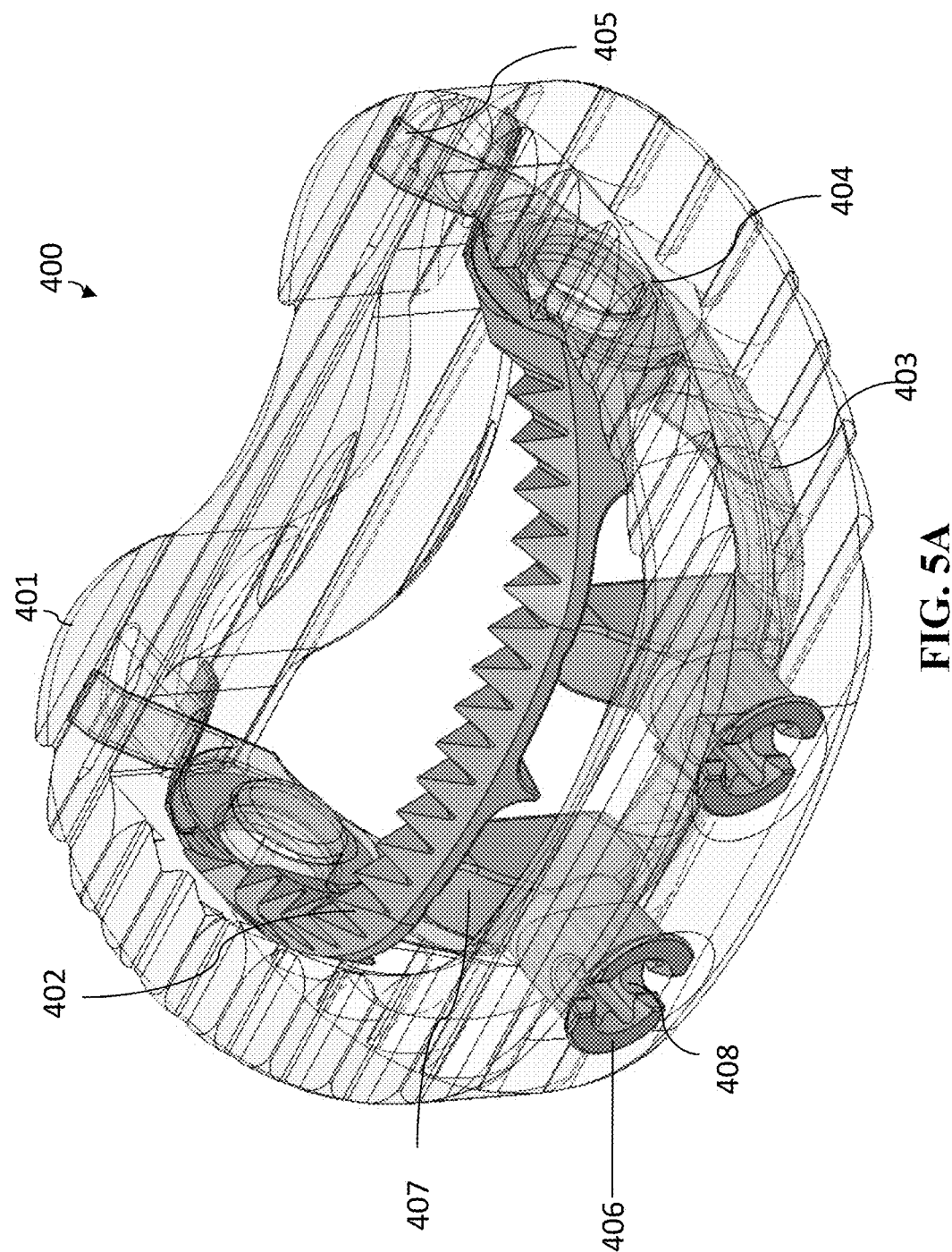
FIG. 5A-5C depict different views of the lumbar cage embodiment of the present invention shown in FIGS. 4A-4C in which the single-opened-height controlled anchoring system is shown in the opened (or anchored) position.
Figure 5B:
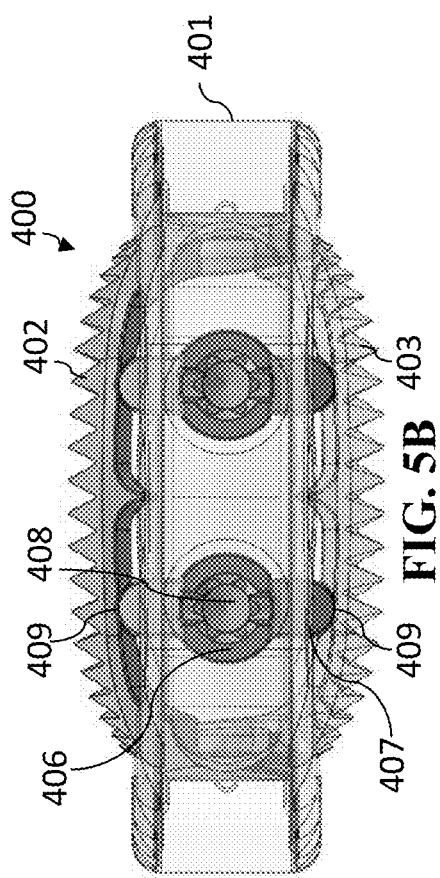
Figure 5C:
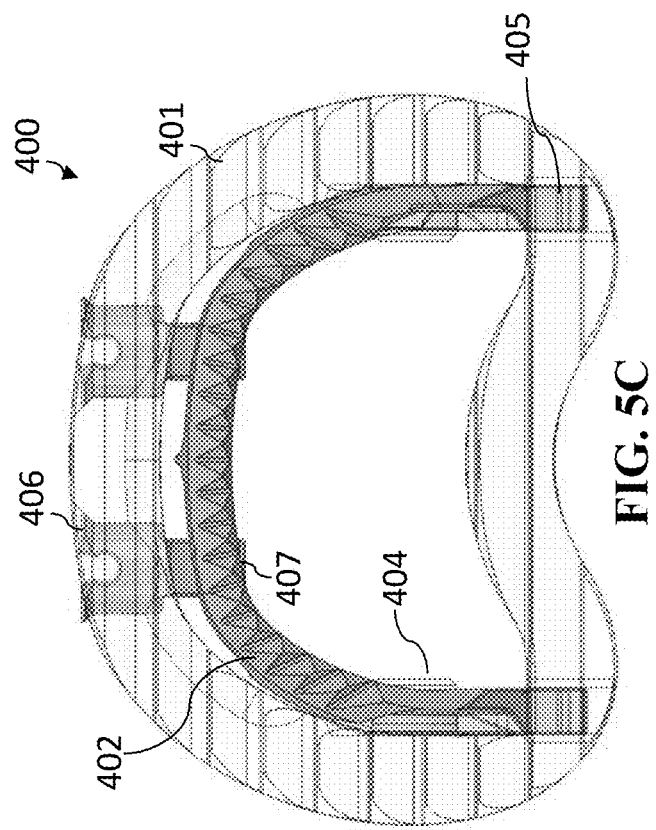

FIGS. 5A-5C show cage 400 in an opened position. In this opened position, spindle 406 has been rotated (generally by around 90 degrees) so that each of the separators 407 are now pushing superior anchoring section 402 and inferior anchoring section 403 outward (i.e., superior anchoring section 402 is being pushed vertically in a superior direction and inferior anchoring section 403 is being pushed vertically in an inferior direction). This movement of superior anchoring section 402 and inferior anchoring section 403 will expand the anchoring system in a vertical direction to anchor cage 400 in place. While this moves the anterior portions of the anchoring sections 402-403 in opposite directions vertically, the height of the cage body 401 does not itself expand. Thus, the anchoring sections 402-403 anchor and secure the cage body 401.

Superior anchoring section 402 and inferior anchoring section 403 have recesses 409 located on the sides contacting the separator 407 so that when positioned to open the jaw mechanism, separator 407 fits into recesses 409. The frictional forces will maintain the separator 407 in such position, which will thus maintain the jaw mechanism open (and the cage body 401 anchored).

As shown in FIGS. 4A-4C and FIGS. 5A-5C, the cage 400 has two spindles 407. This generally is because of the size of a lumbar cage. However, the lumbar cage can be utilized with only one spindle to move and maintain the jaw mechanism in an open position. Moreover the cage can be a cervical cage, which generally has one spindle (although, it too can have two spindles, if so desired).

Figure 6A:
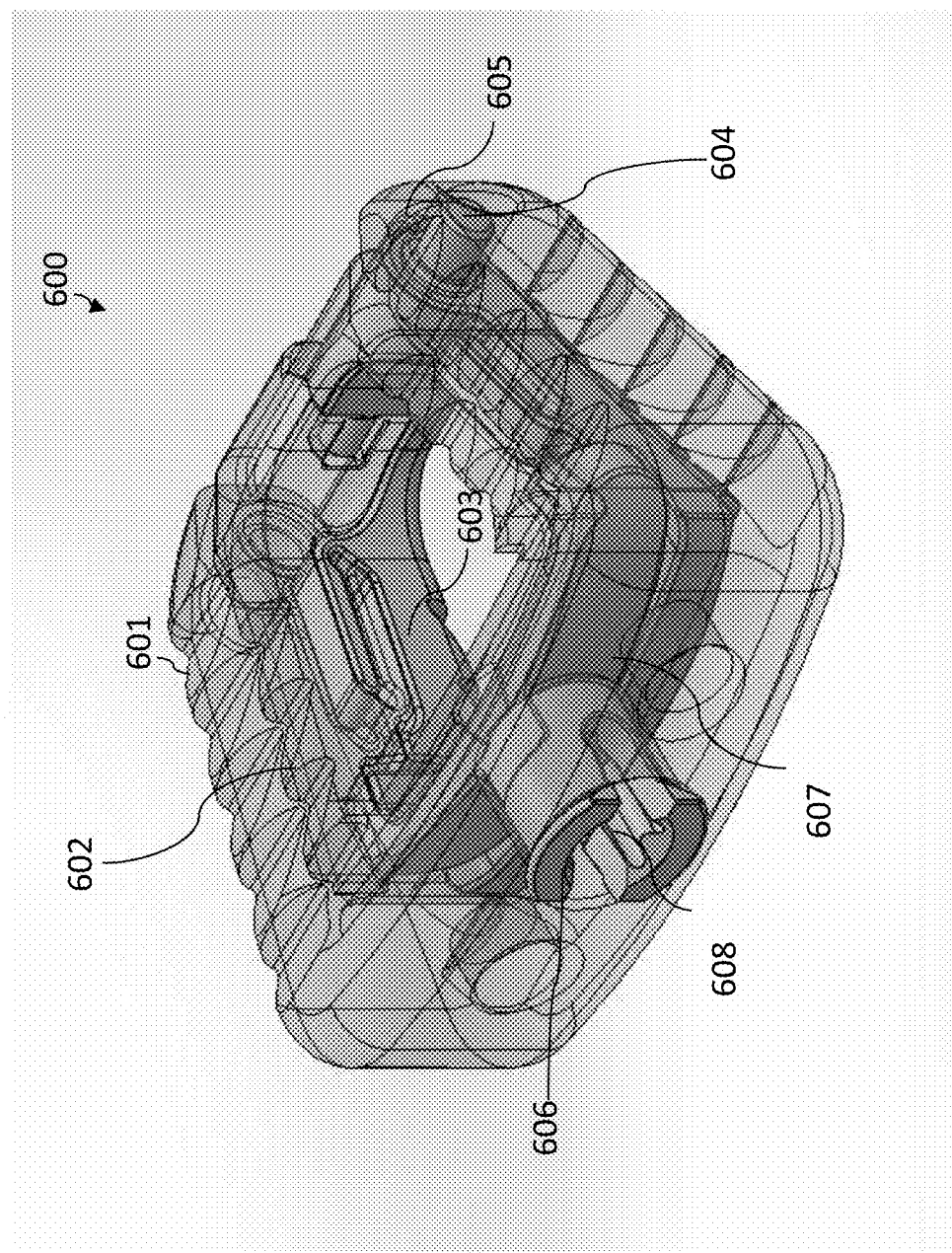
FIG. 6A-6D depict a cervical embodiment of the present invention having a single-opened-height controlled anchoring system that is in the closed (or unanchored) position, which embodiment has similarities in its design to that of the lumbar cage embodiment shown in FIGS. 4A-4C and 5A-5C.
Figure 6C:
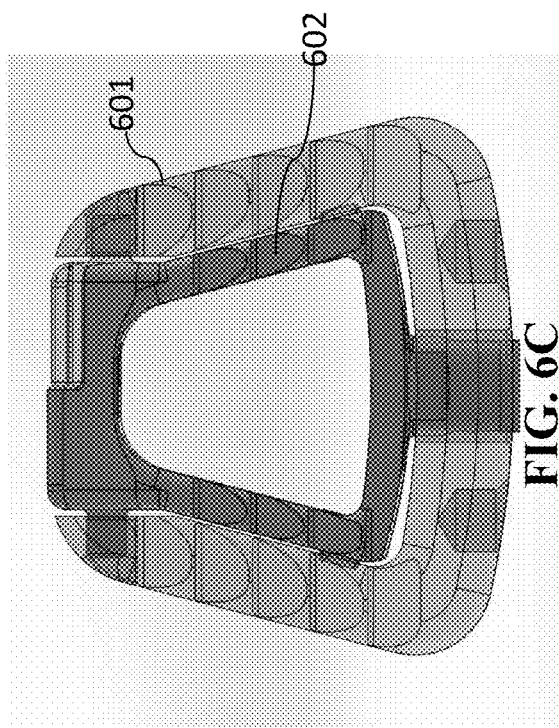
Figure 6B:
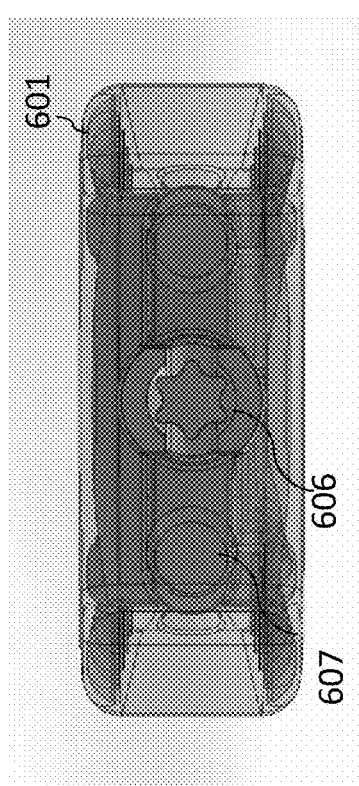
Figure 6D:
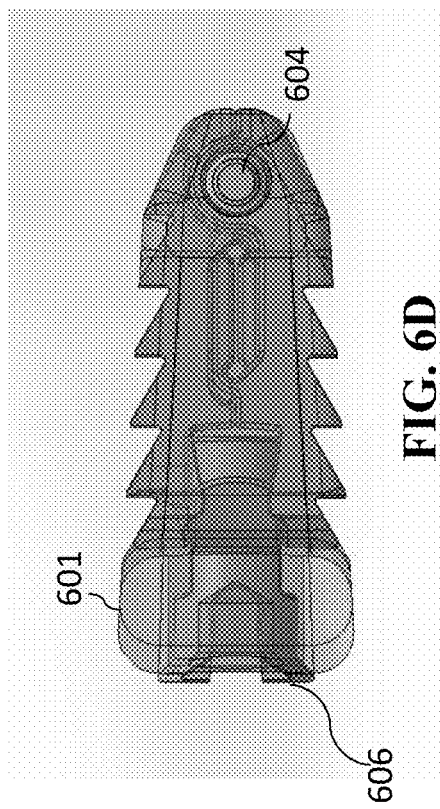
Figure 7A:
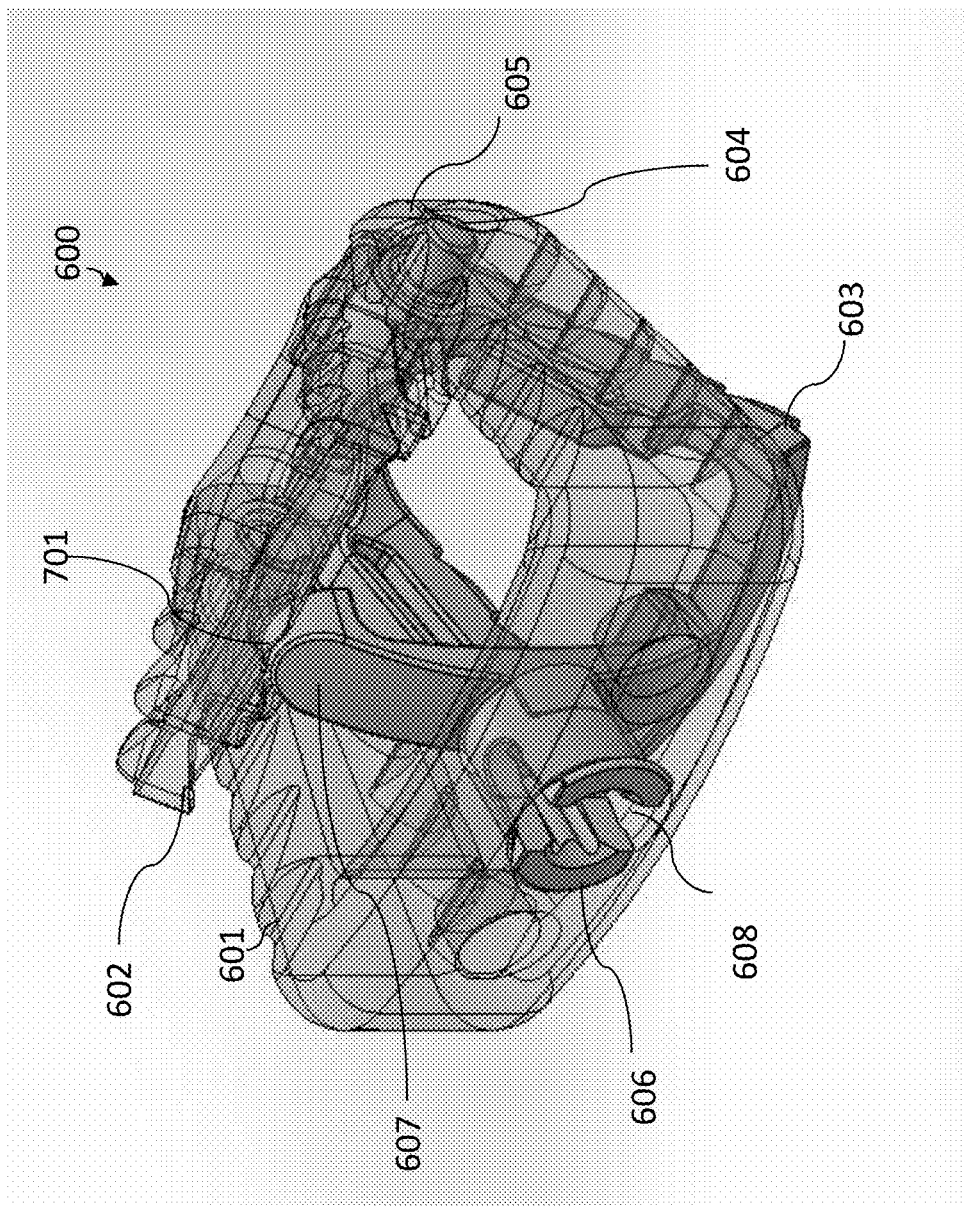
FIG. 7A-7D depict different views of the cervical cage embodiment of the present invention shown in FIGS. 6A-6D in which the single-opened-height controlled anchoring system is shown in the opened (or anchored) position.
Figure 7C:
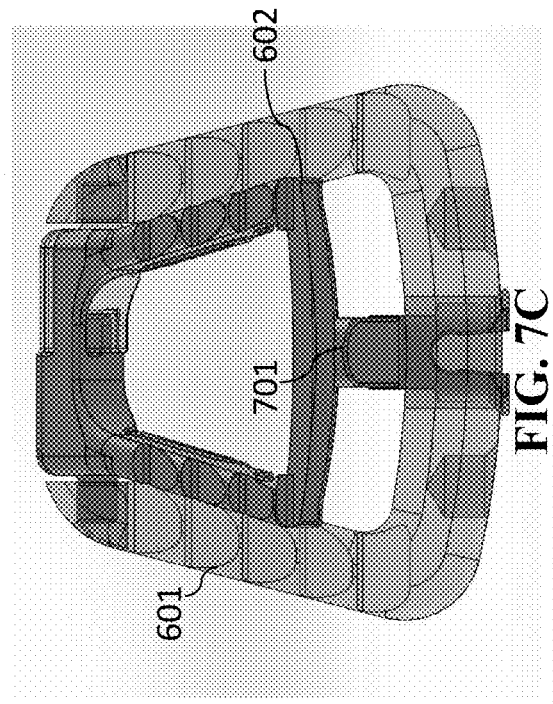
Figure 7B:
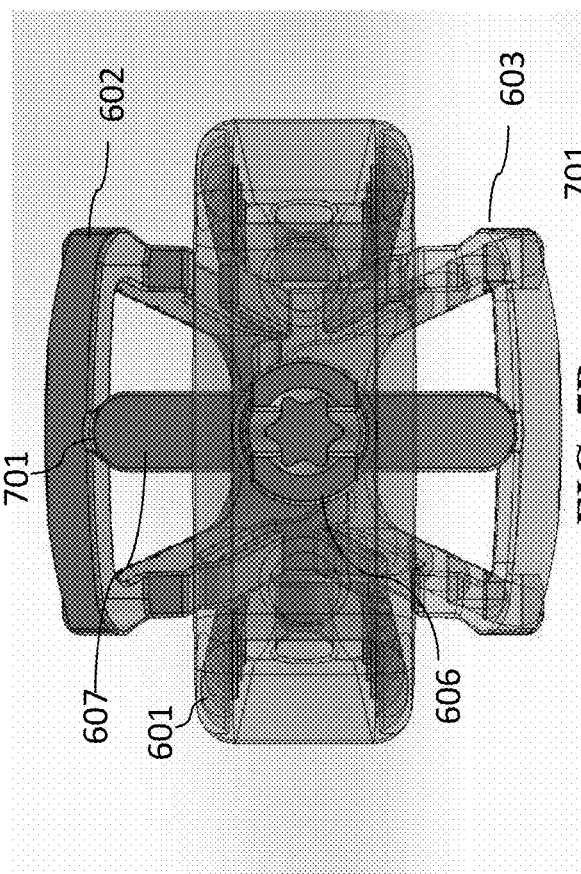
Figure 7D:
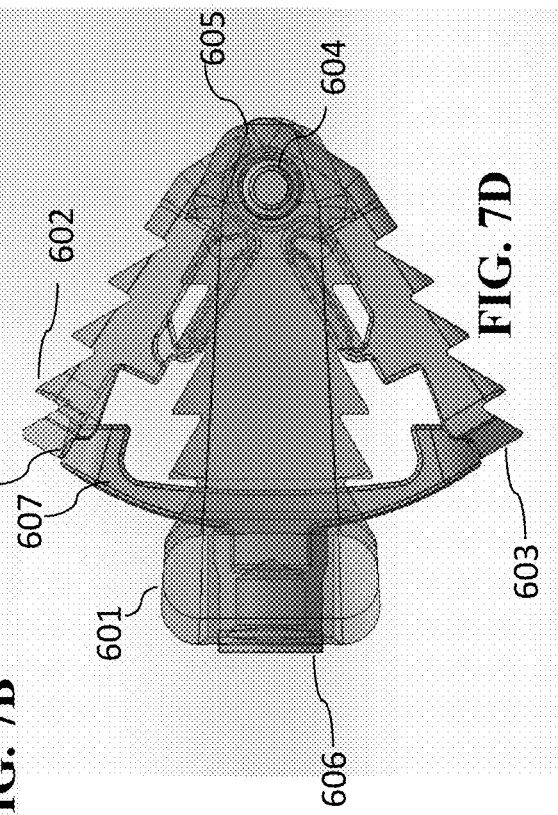

A second embodiment having a single-opened-height controlled anchoring system is illustrated in FIGS. 6A-6D and FIGS. 7A-7D. This embodiment is similar to that of cage 400, except that the cage 600 is a cervical cage embodiment having only one spindle in the single-opened-height controlled anchoring system. Again, cervical cage embodiments generally will have one spindle, which lumbar cage embodiments will have two spindles. The views of FIGS. 6A-6D and FIGS. 7A-7D are as follows (a) each of FIGS. 6A and 7A are perspective views of cage 600, (b) each of FIGS. 6B and 7B are anterior views of cage 600, (c) each of FIGS. 6C and 7C are superior/inferior views of cage 600, and (d) each of FIGS. 6D and 7D are sagittal views of cage 1100 (with the anterior portion of cage 600 depicted toward the left in FIGS. 6D and 7D). (The superior/inferior views are interchangeable in this embodiment, because the device is symmetric and the superior/inferior view is dependent upon the orientation of the cage 600.

FIGS. 6A-6D show the cage 600 in the closed (i.e., unanchored) form. Cage 600 has a cage body 601 and a jaw mechanism. The jaw mechanism has superior jaw section 602 and inferior jaw section 603 that are pivotably connected to one another at pivot joint 604. On the other side of the pivot joint 604, the superior jaw section 602 and inferior jaw section 603 have end portions 605. Similar to cage 400 shown in FIGS. 4A-4C and FIGS. 5A-5C, these are spring loaded so that the forces are compressing superior jaw section 602 and inferior jaw section 603 toward one another. Cage 600 further has a spindle 606 having a separator 607 and a central feature 608 that is operable to accept a rotational tool, so that spindle 606 can be rotated.

FIGS. 7A-7D show the cage 600 in the opened (i.e., anchored) form. Superior jaw section 602 and inferior jaw section 603 have recesses 701 (located in the anterior portions of superior jaw section 602 and inferior jaw section 603) in which separator 607 fits when the jaw mechanism is positioned in the open position. Again, the frictional forces will maintain the separator 607 in such position, which will thus maintain the jaw mechanism open (and the cage 600 anchored). Optionally, a slot ring (such as shown in FIGS. 12A-12E, and FIGS. 13A-13F, discussed below) can be utilized to maintain the jaw mechanism open.

Figure 1:
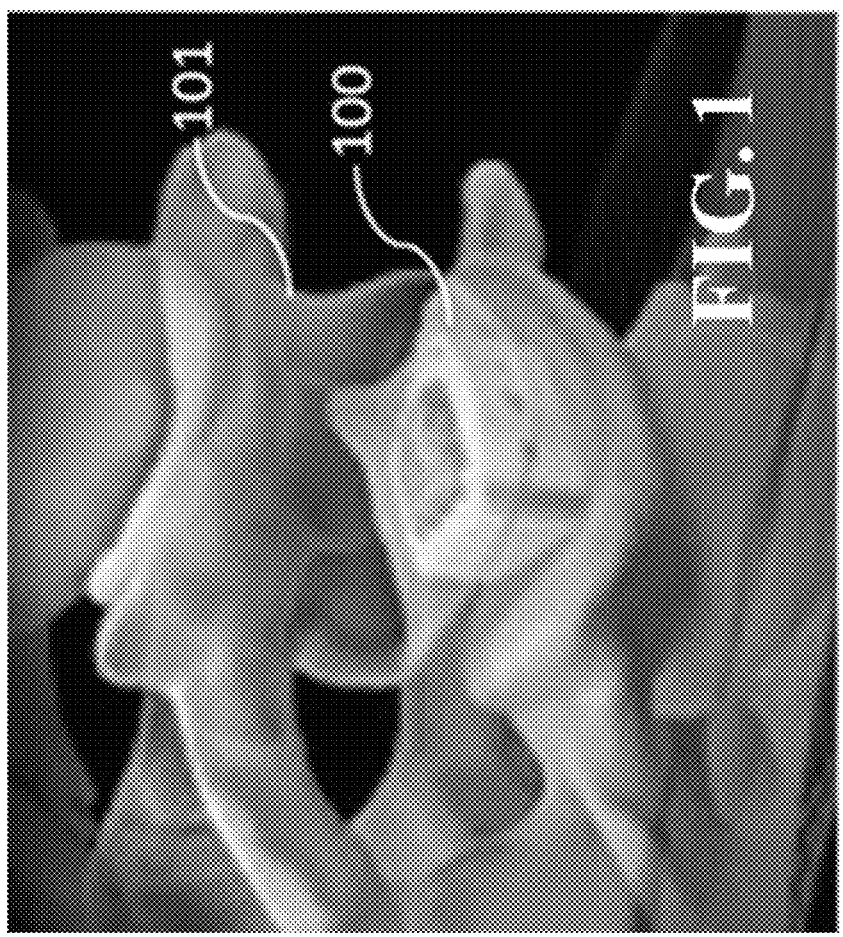
FIG. 1 depicts a prior art cage inserted in a spinal column.
Figure 2:
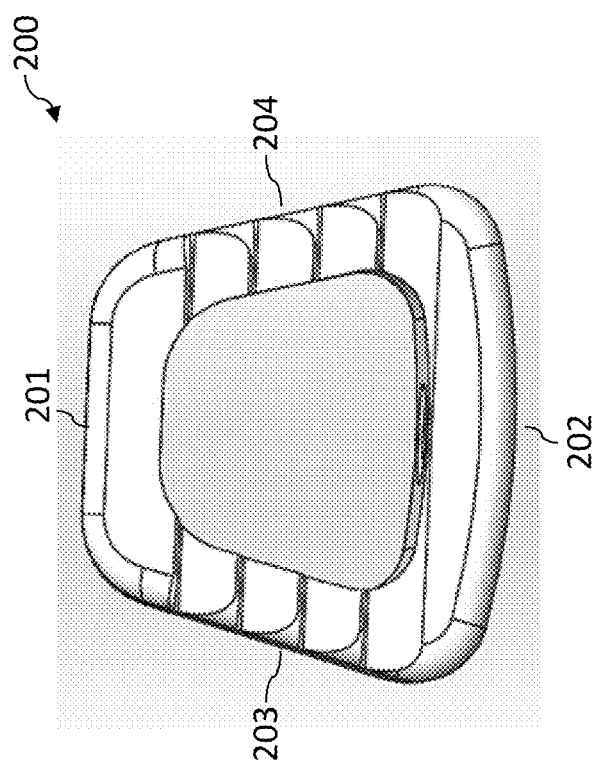
FIG. 2 depicts a prior art, non-expandable cage.
Figure 3B:
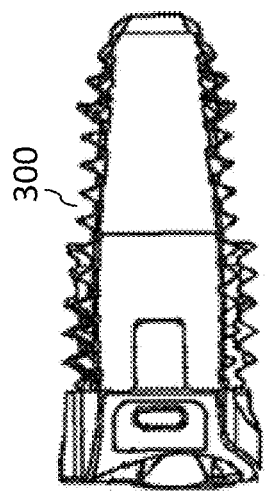
FIGS. 3A-3C depict different views of a prior art, non-expandable cage.
Figure 3C:
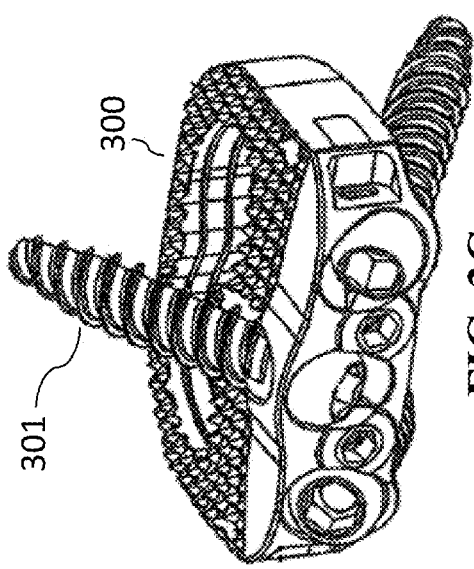
Figure 3A:
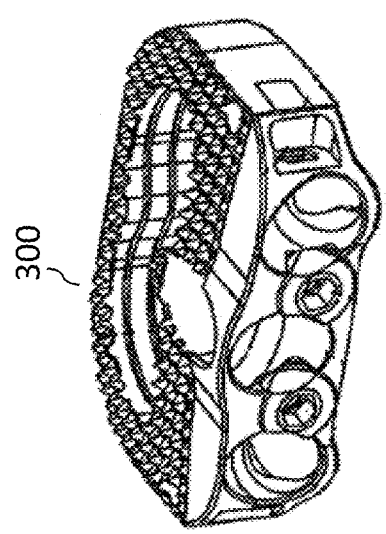

While not shown in FIGS. 4A-4C, FIGS. 5A-5C, FIGS. 6A-6D, and FIGS. 7A-7D the cage embodiments can include holes through which other fasteners (such as screws) can then be inserted for further securing of the device. Such holes and fasteners are illustrated in FIGS. 3A-3C. Since the cages 400 and 600 can be anchored and secured prior to the insertion of these additional fasteners (using the anchoring systems), this provides additional freedom for the surgeon or other practitioner to properly insert and secure these fasteners because the cage is already being anchored.

Cage Embodiments with Variable-Opened-Height Controlled Anchoring Systems

Figure 8A:
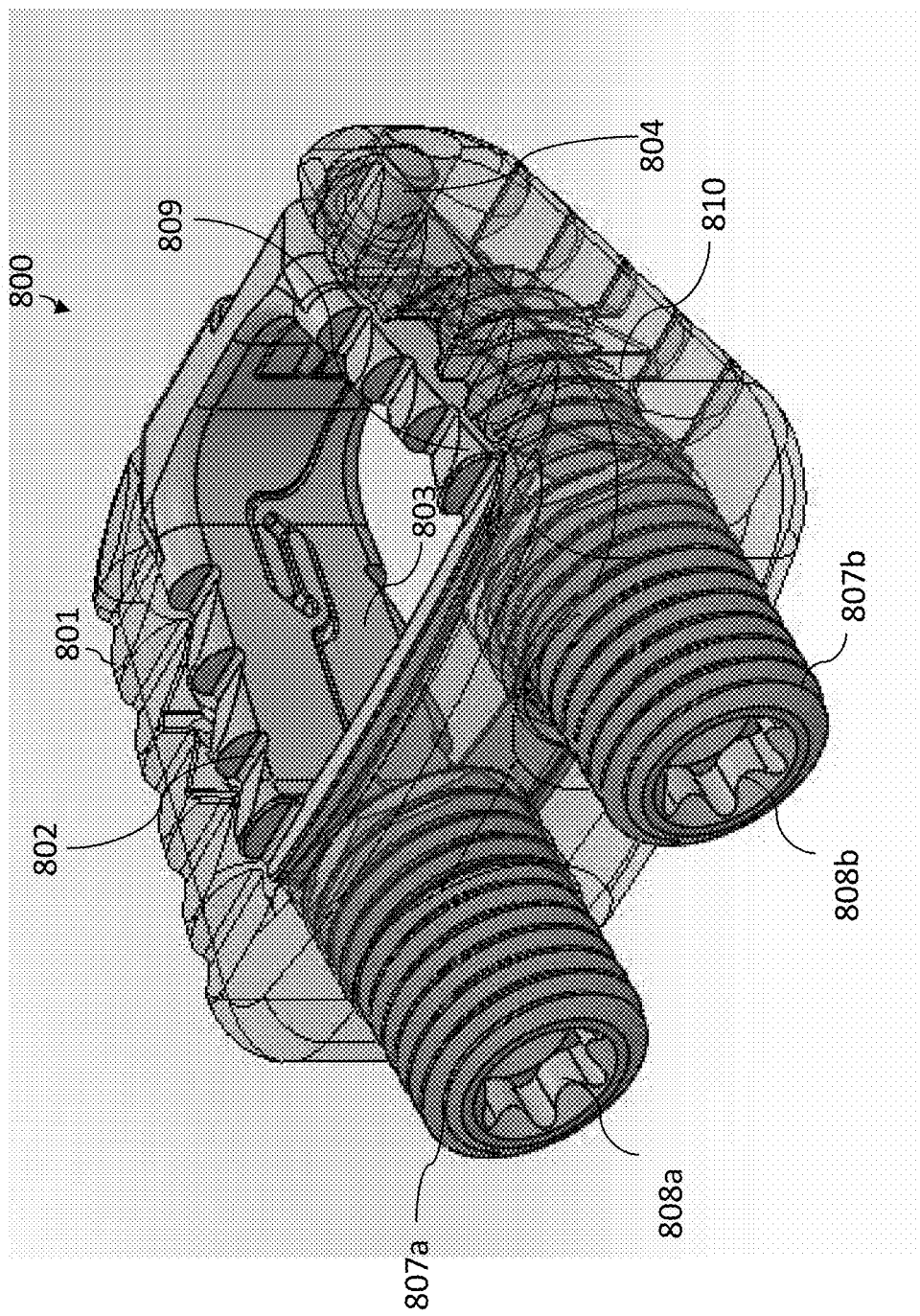
FIGS. 8A-8D depict different views of an alternative cervical cage embodiment of the present invention in which the anchoring system is a variable-opened-height controlled anchoring system shown in the closed (or unanchored) position.
Figure 8C:
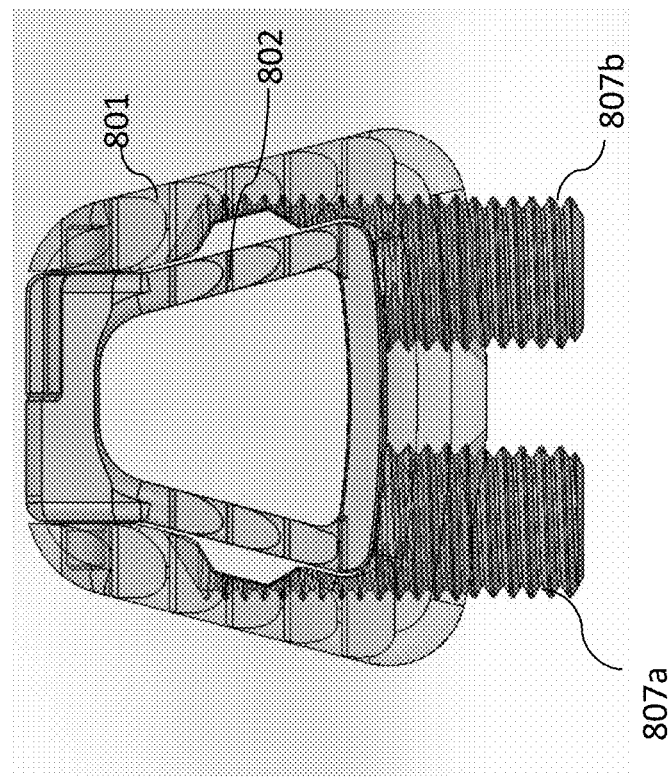
Figure 8B:
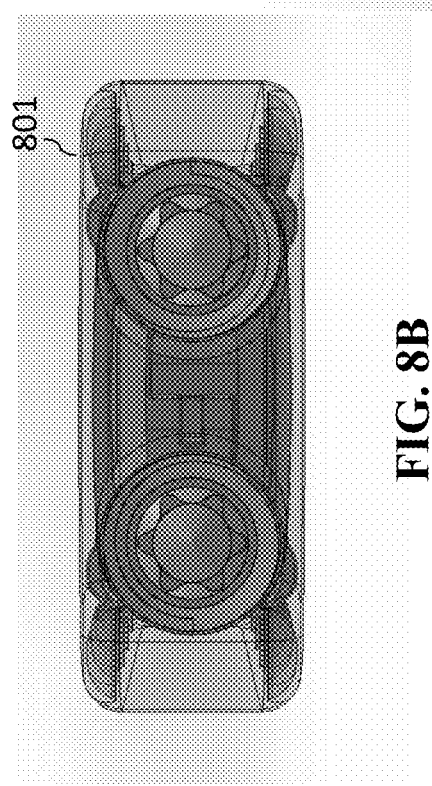
Figure 8D:
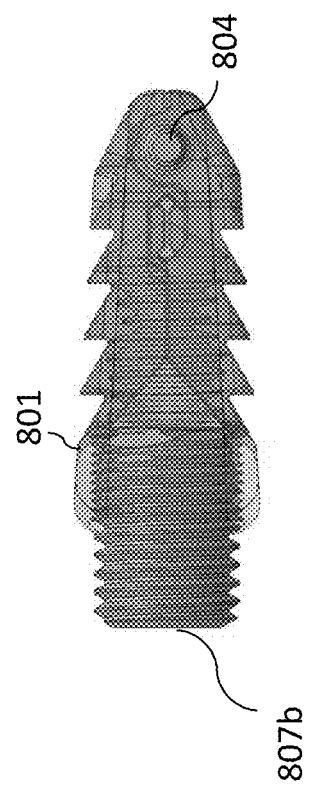

Referring to the figures, another embodiment of the present invention in FIGS. 8A-8D, 9A-9D, 10A-10D, and 11A-11D, which is a cervical cage embodiment having a variable-opened-height controlled anchoring system. FIGS. 8A-8D depict different views of cage 800 embodiment of the present invention in which the variable-opened-height controlled anchoring system is in the closed (or unanchored) position. The perspectives of FIGS. 8A-8D are, respectively, FIG. 8A is a perspective view, FIG. 8B is an anterior view, FIG. 8C is a superior/inferior view, and FIG. 8D is a sagittal view (with the anterior portion of cage 800 depicted toward the left in the figure).

Figure 9A:
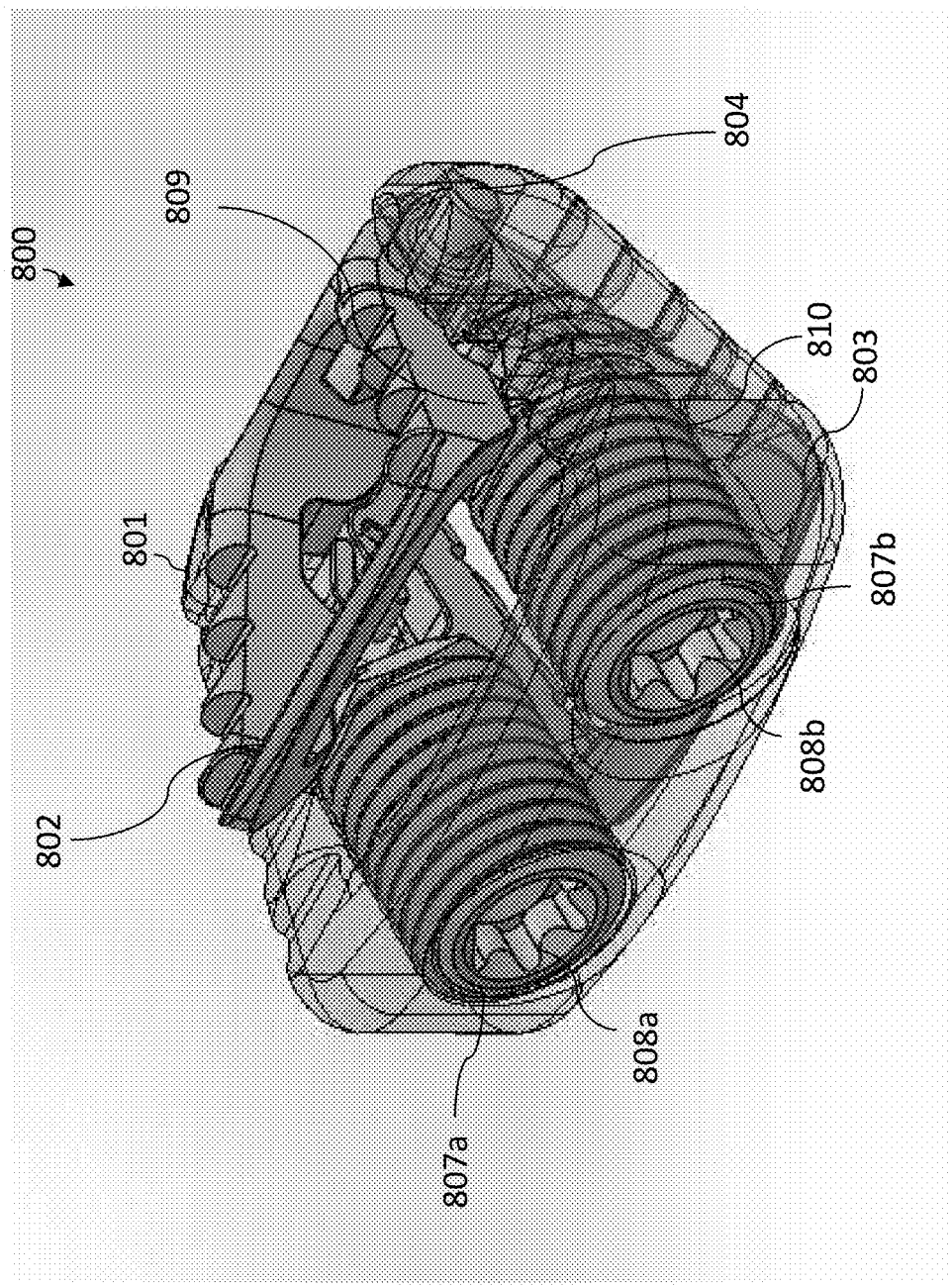
Figure 10B:
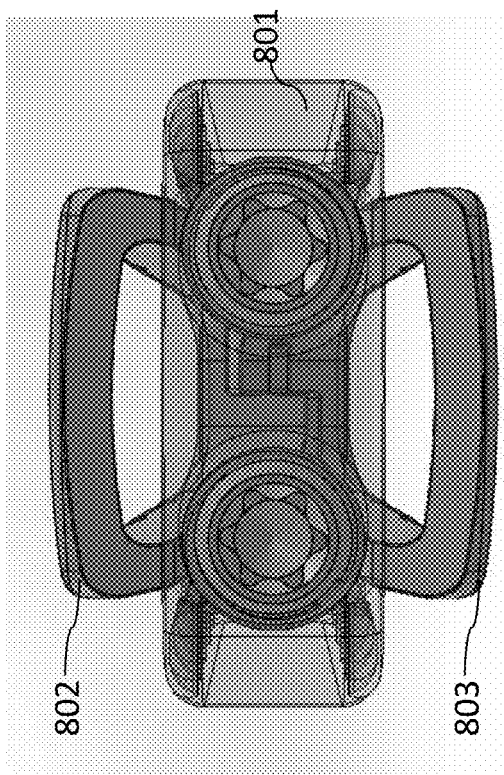
FIGS. 10A-10D depict different views of the alternative cervical cage embodiment of the present invention shown in FIGS. 8A-8D in which the variable-opened-height controlled anchoring system is shown in an opened (or anchored) position (in which the anchoring system is more partially opened as compared to the views shown in FIGS. 9A-9D).
Figure 10D:
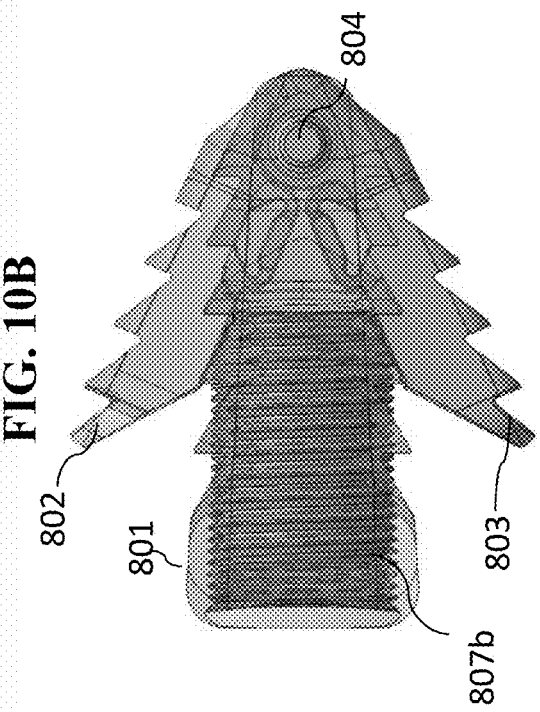
Figure 10A:
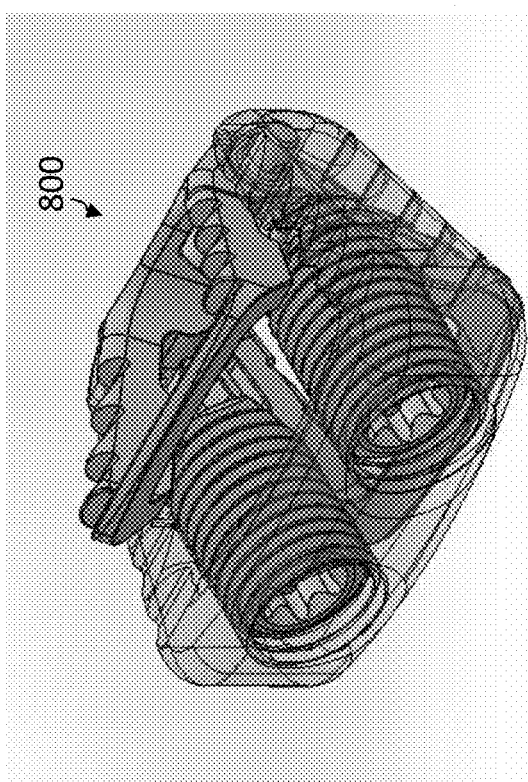
Figure 10C:
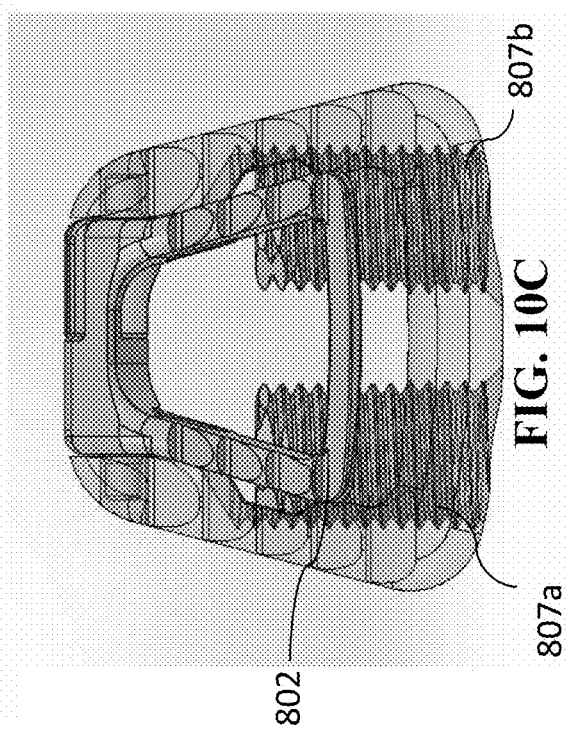
Figure 11B:
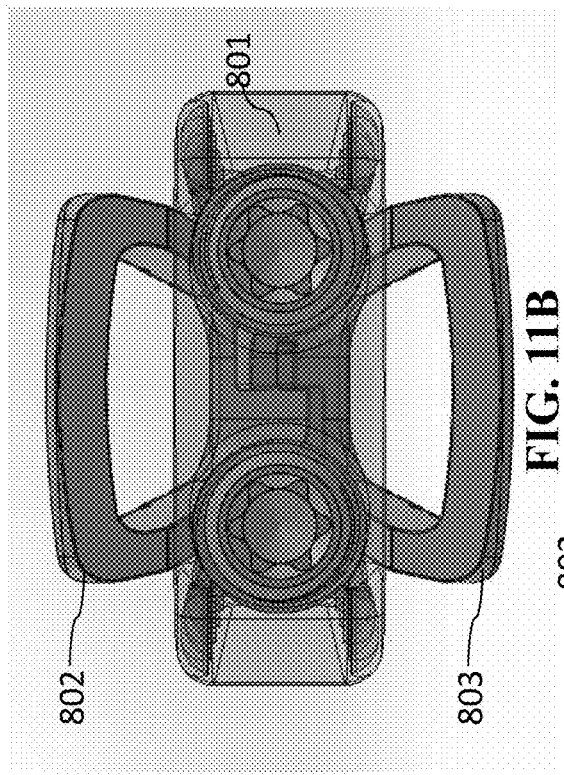
FIGS. 11A-11D depict different views of the alternative lumbar cage embodiment of the present invention shown in FIGS. 11A-11D in which the variable-opened-height controlled anchoring system is shown in an opened (or anchored) position (in which the anchoring system is completely opened and further opened as compared to the views shown in FIGS. 9A-9D and FIGS. 10A-10D).
Figure 11D:
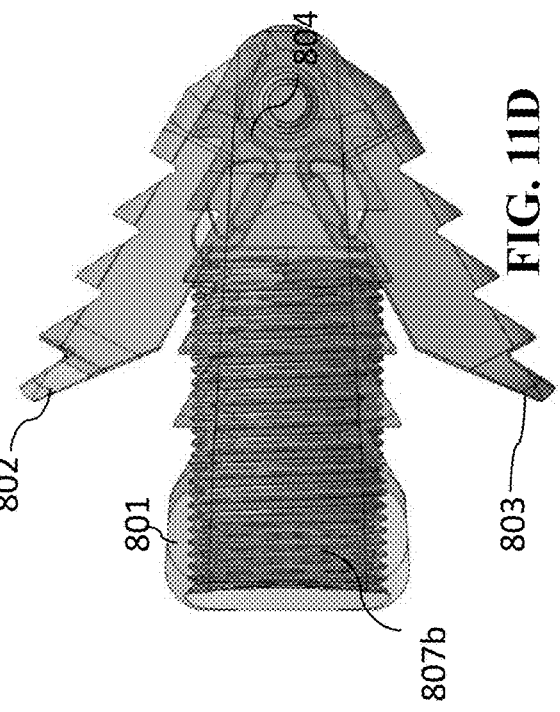
Figure 11A:
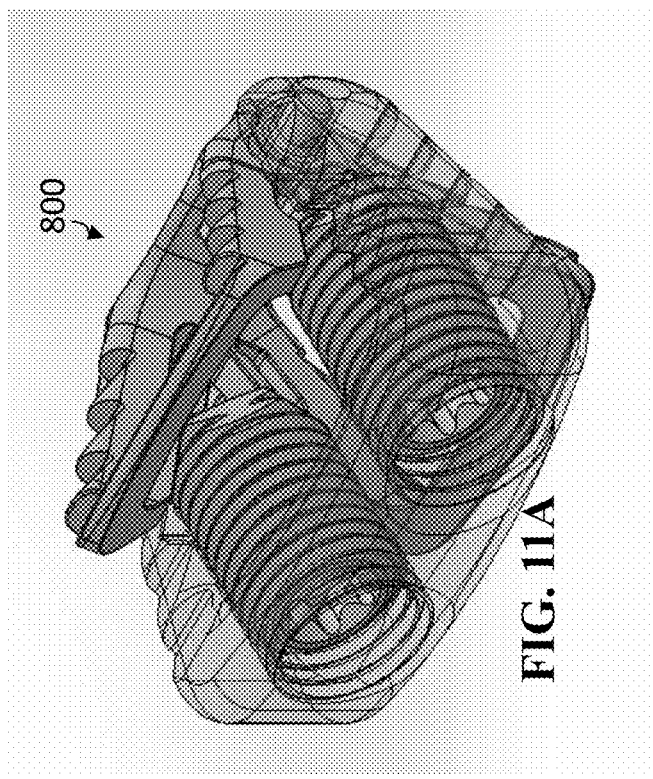
Figure 11C:
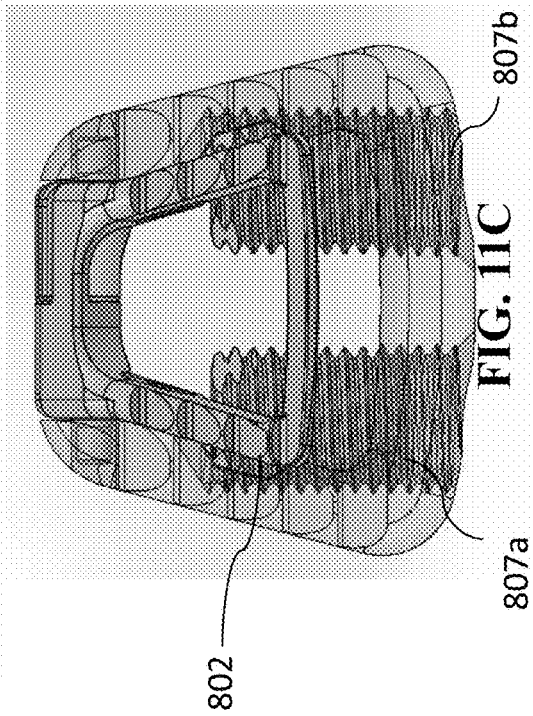

The corresponding views are depicted in FIGS. 9A-9D, FIGS. 10A-10D, and FIGS. 11A-11D. I.e., (a) each of FIGS. 9A, 10A, and 11A are perspective views of cage 800, (b) each of FIGS. 9B, 10B, and 11B are anterior views of cage 800, (c) each of FIGS. 9C, 10C, and 11C are superior views of cage 800, and (d) each of FIGS. 9D, 10D, and 11D are sagittal views of cage 800. Unlike FIGS. 8A-8D, each of FIGS. 9A-9D, FIGS. 10A-10D, and FIGS. 11A-11D show cage 800 in various degrees of heights of the anchoring system in the opened position (with the height progressively greater for cage 800 as each of FIGS. 9A-9D, FIGS. 10A-10D, and FIGS. 11A-11D). By way of example, FIGS. 9A-9D can be depicting a height of 9 mm, FIGS. 10A-10D can be depicting a height of 10 mm, and FIGS. 11A-11D can be depicting a height of 11 mm. Such height of the anchoring system is measured from the anterior portions of the superior anchoring section 802 and inferior anchoring system 803.

Referring to FIG. 8A, this reflects similarities in cage 800 components with that of cage 400. Similar to cage 400, cage 800 has cage body 801, superior anchoring section 802, inferior anchoring section 803, and pivot joint 804. However, the driving mechanism for the changing the height of the variable-controlled anchoring system is performed with one or more lead screws. Cage 800 is shown with two lead screws 807a and 807b. Lead screws 807a and 807b also each have a central feature 808a and 808b, respectively, that are operable to accept a rotational tool, so that each of lead screws 807a and 807b can be rotated. Lead screws 807a and 807b can be rotated independently from one another.

Superior anchoring section 802 includes recesses 809 and inferior anchoring section 803 includes recesses 810 that come in contact with a lead screw (such as lead screw 808b) such that when lead screw 807b is rotated, the superior anchoring section 802 and inferior anchoring section 803 will pivot at pivot joint 804, allowing the anterior portion of superior anchoring section 802 to move vertically with respect to the anterior portion of inferior anchoring section. By such rotation of the lead screws 808a and 808b, the anchoring system can be varied in height.

This change in height of cage 800 is depicted progressively in FIGS. 9A-9D, FIGS. 10A-10D, and FIGS. 11A-11D. In FIGS. 9A-9D, cage 800 is shown in a partially opened position in which, lead screws 807a and 807b have been rotated so that they are partially inserted into cage 800. This has caused the portion of superior anchoring section 802 and inferior anchoring section 803 to pivot at pivot joint 804, which has resulted in the anterior portion of superior anchoring section 802 to move vertically with respect to the anterior portion of inferior anchoring section 803. This resulting height is more clearly seen in the anterior view of FIG. 9B and the sagittal view of FIG. 9D. Again, for example, in cage 800 in FIGS. 9A-9D, this height can be 9 mm.

FIGS. 10A-10D depict that lead screws 807a and 807b have been further rotated so that they are further partially inserted into cage 800. This has resulting in in the anterior portion of superior anchoring section 802 to move even further vertically with respect to the anterior portion of inferior anchoring section 803. This resulting height is more clearly seen in the anterior view of FIG. 10B and the sagittal view of FIG. 10D. Again, for example, in cage 800 in FIGS. 10A-10D, this height can be 10 mm.

FIGS. 11A-11D depict that lead screws 807a and 807b have been further rotated so that they are completely inserted into cage 800. This has resulting in in the anterior portion of superior anchoring section 802 to move even further vertically with respect to the anterior portion of inferior anchoring section 803. This resulting height is more clearly seen in the anterior view of FIG. 11B and the sagittal view of FIG. 11D. Again, for example, in cage 800 in FIGS. 11A-11D, this height can be 11 mm.

By the rotation of lead screws 807a and 807b, the height of the anchoring system can be controllably varied.

Alternatively, a variable-opened-height controlled anchoring system with one lead screw can be utilized.

A second embodiment having a variable-opened-height controlled anchoring system is illustrated in FIGS. 12A-12E and FIGS. 13A-13F. This embodiment of FIGS. 12A-12E and FIGS. 13A-13F (cage 1200) has similarities with respect to the single-opened-height controlled anchoring systems shown in FIGS. 4A-4C, FIGS. 5A-5C, FIGS. 6A-6D, and FIGS. 7A-7D, except that for the variable-opened-height controlled anchoring system of cage 1200 the spindle 1206 (or multiple spindles as the case may be) having separators 1207 that can be positioned in partially opened positions based upon the recesses (such as recesses 1301 and recesses 1302). Once moved to the appropriate setting (for the desired vertical size to be opened), the slot ring 1209 can then be positioned to prevent the spindle 1206 from further movement.

Figure 12A:
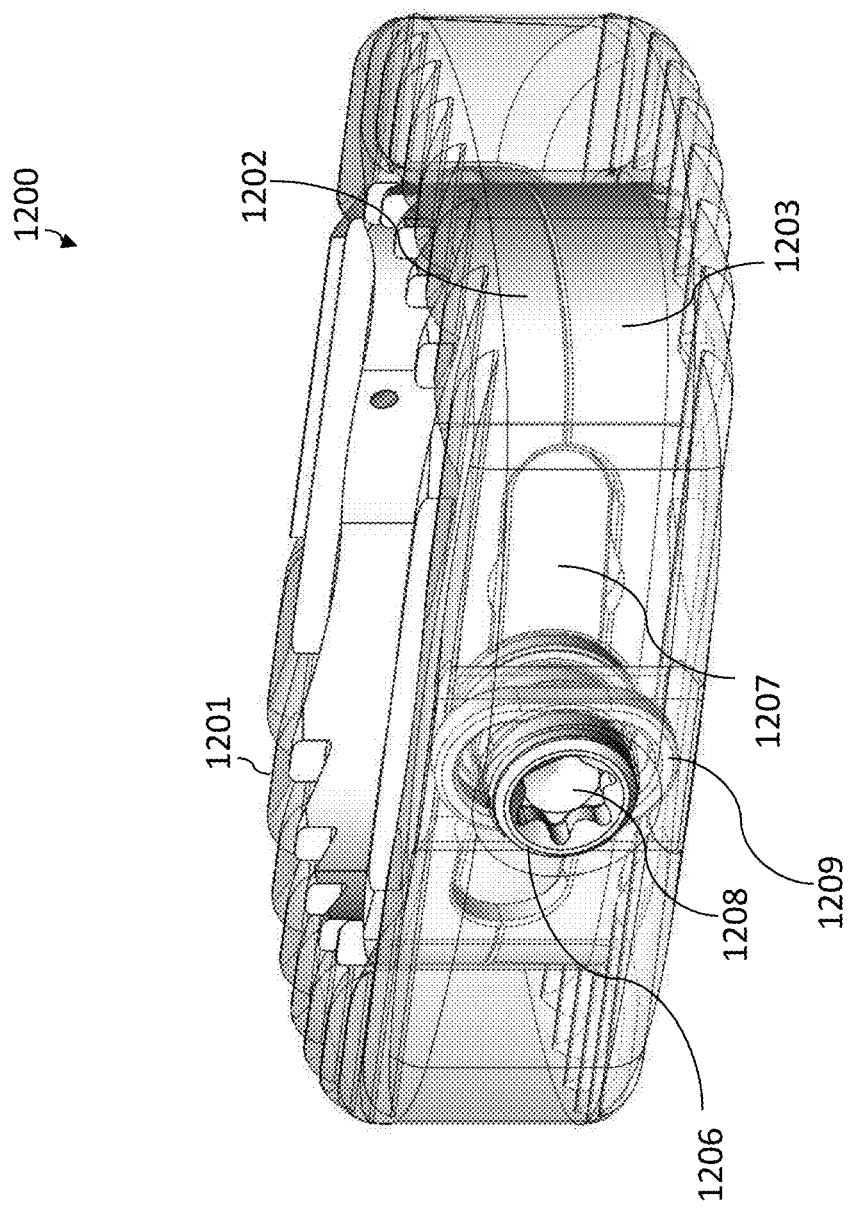
FIG. 12A-12E depict a lumbar embodiment of the present invention having a single-opened-height controlled anchoring system that is in the closed (or unanchored) position, which embodiment has similarities in its design to that of the lumbar cage embodiment shown in FIGS. 4A-4C and 5A-5C.
Figure 12B:
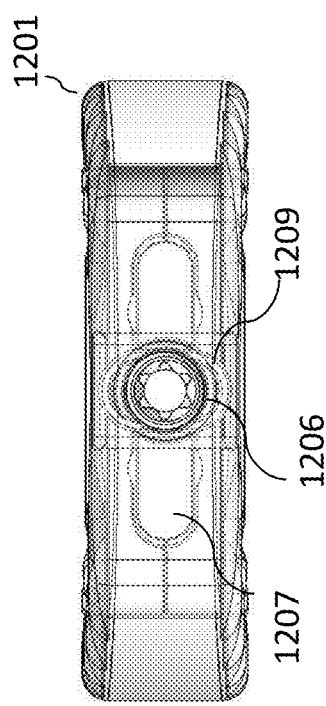
Figure 12C:
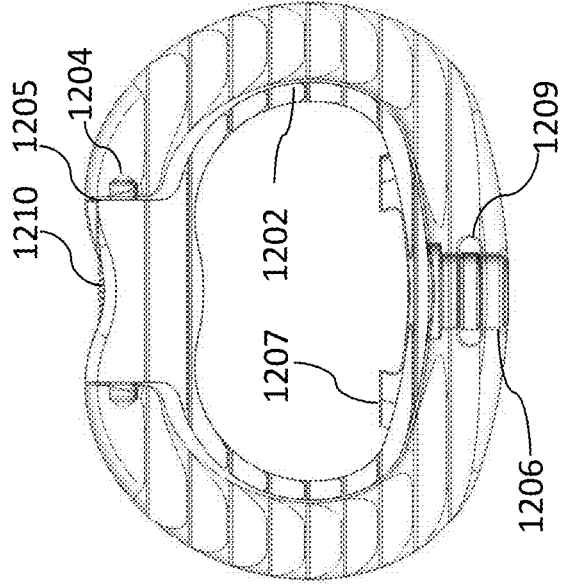
Figure 12D:
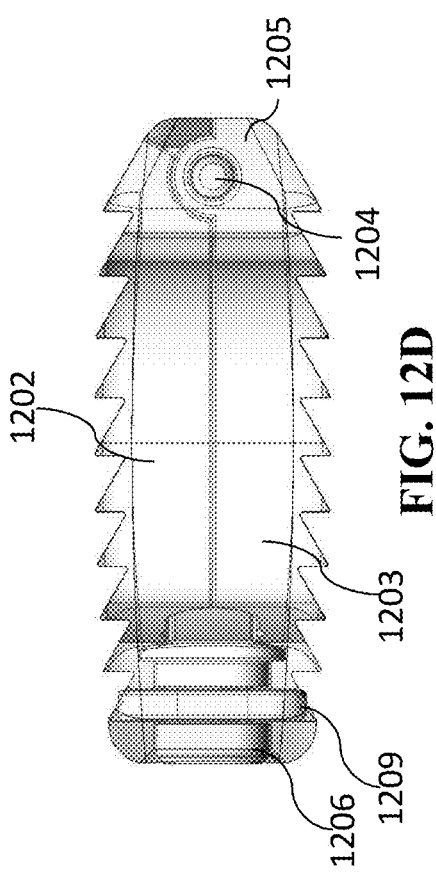
Figure 12E:
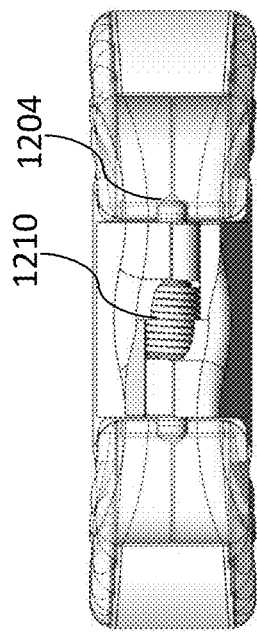
Figure 13A:
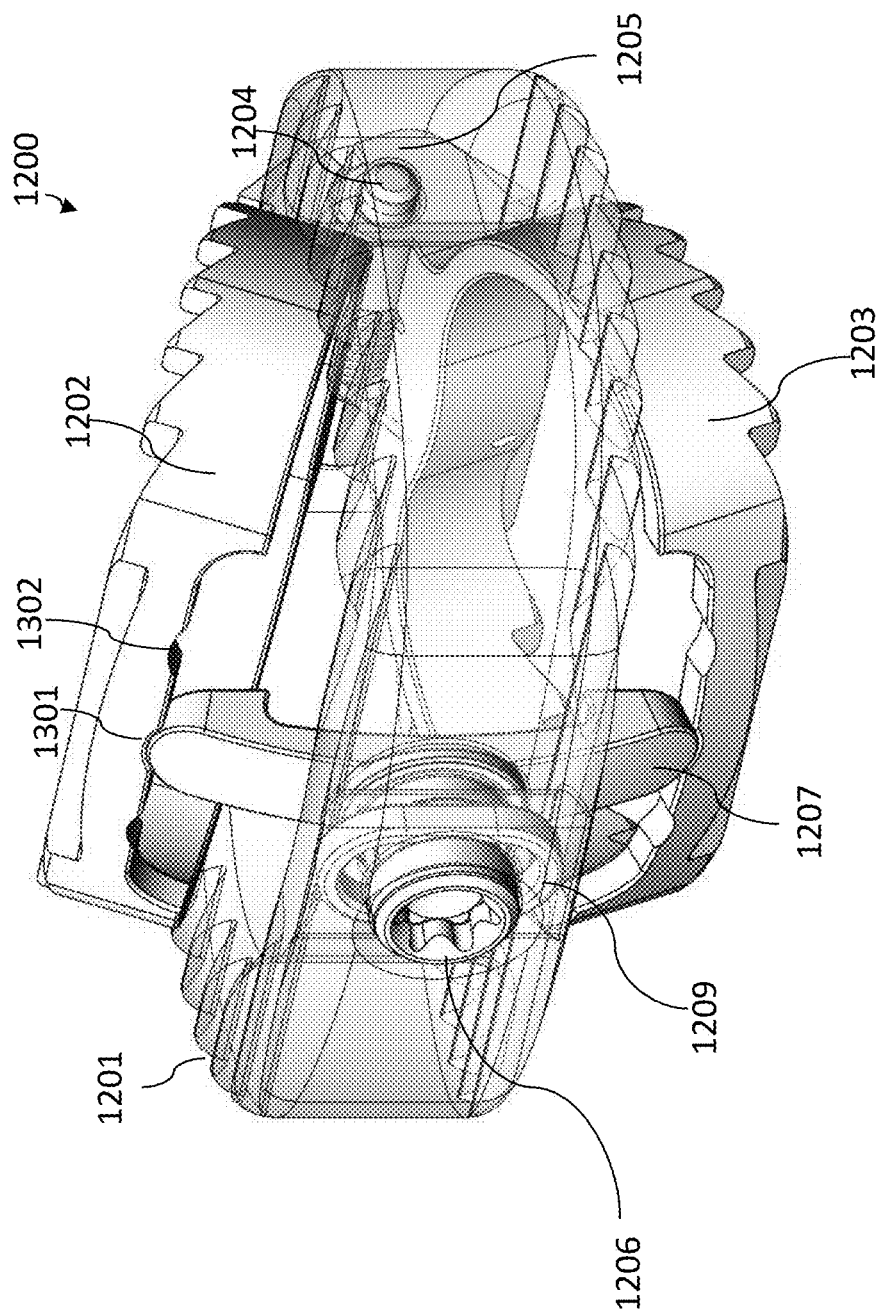
FIGS. 13A-13F depict different views of the lumbar cage embodiment of the present invention shown in FIGS. 12A-12E in which the single-opened-height controlled anchoring system is shown in the opened (or anchored) position.
Figure 13C:
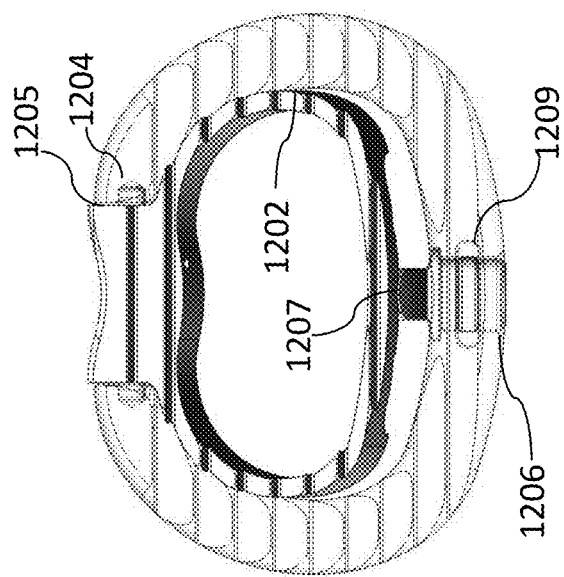
Figure 13E:
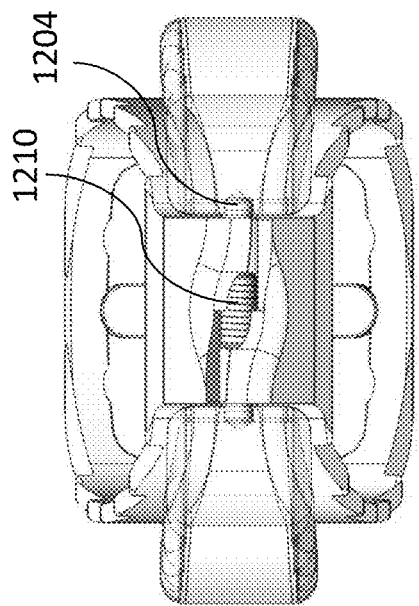
Figure 13B:
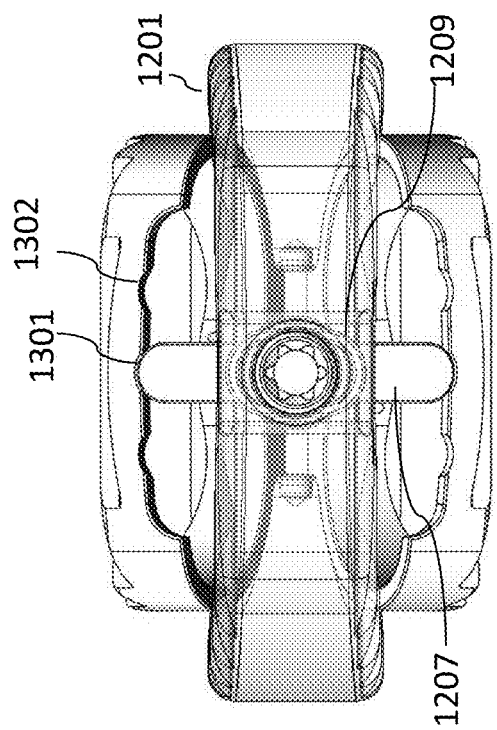
Figure 13D:
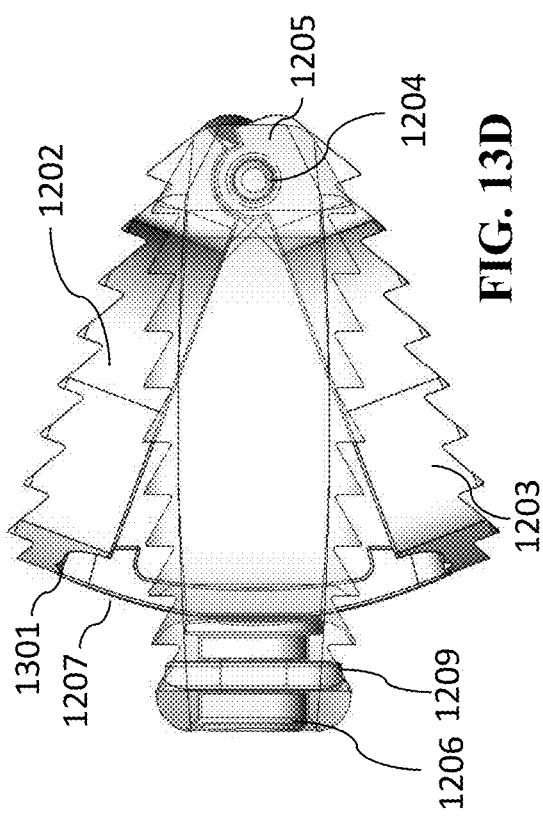
Figure 13F:
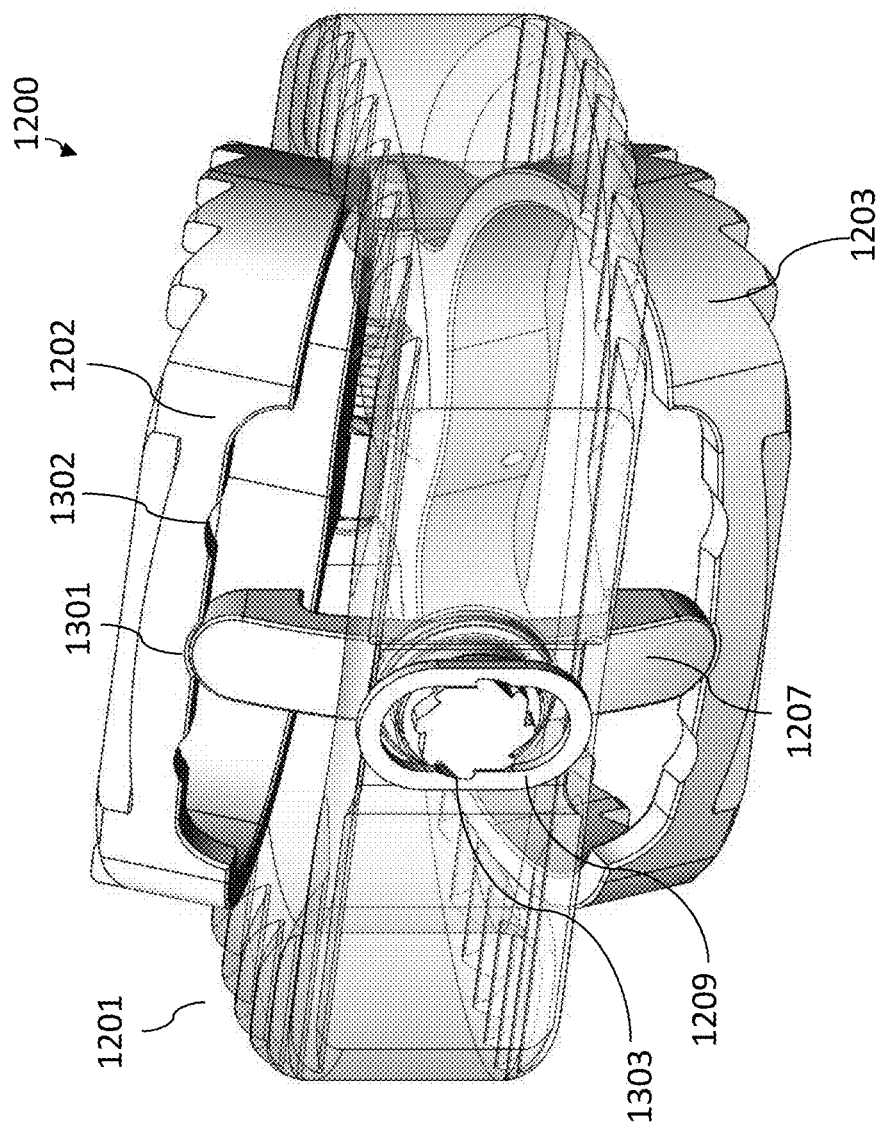

The views of FIGS. 12A-12E and FIGS. 13A-13F are as follows (a) each of FIGS. 12A and 13A are perspective views of cage 1200, (b) each of FIGS. 12B and 13B are anterior views of cage 1200, (c) each of FIGS. 12C and 13C are superior/inferior views of cage 1200, (d) each of FIGS. 12D and 13D are sagittal views of cage 1200 (with the anterior portion of cage 1200 depicted toward the left in FIGS. 12D and 13D), (e) each of FIGS. 12E and 13E are posterior views of cage 1200, and (f) FIG. 13F is a perspective view of a cross section of cage 1200.

FIGS. 12A-12E show the cage 1200 in the closed (i.e., unanchored) form. Cage 1200 has a cage body 1201 and a jaw mechanism. The jaw mechanism has superior jaw section 1202 and inferior jaw section 1203 that are pivotably connected to one another at pivot joint 1204. On the other side of the pivot joint 1204, the superior jaw section 1202 and inferior jaw section 1203 have end portions 1205. Similar to cages 400 and 600 shown in (a) FIGS. 4A-4C and FIGS. 5A-5C and (b) FIGS. 6A-6D, and FIGS. 7A-7D, respectively, these are spring loaded (with spring 1210) so that the forces are compressing superior jaw section 1202 and inferior jaw section 1203 toward one another. Cage 1200 further has a spindle 1206 having a separator 1207 and a central feature 1208 that is operable to accept a rotational tool, so that spindle 1206 can be rotated. Cage 1200 also includes a slot ring 1209 that can be used to lock the spindle 1206 in place to maintain the jaw mechanism in the desired position.

FIGS. 13A-13F show the cage 1200 in one of the opened (i.e., anchored) forms (and, as shown, the fully-opened position). Superior jaw section 1202 and inferior jaw section 1203 have recesses 1301 (located in the anterior portions of superior jaw section 1202 and inferior jaw section 1203) in which separator 1207 fits when the jaw mechanism is positioned in the full open position. Again, the frictional forces will maintain the separator 1207 in such position, which will thus maintain the jaw mechanism open (and the cage 1200 anchored). In this embodiment, the slot ring 1209 can be utilized to maintain the jaw mechanism open. The slot ring 1209 in the locked position is shown in FIG. 13F (as shown in cross-section cut along the plane of slot ring 1209, which are locked using spindle serrations 1303 that engage with catch teeth of the slot ring 1209).

Unlike cage 600, cage 1200 is a variable-opened-height controlled anchoring system in that the separator 1207 can be positioned within other recesses, such as recesses 1302. When, separator 1207 is positioned in recesses 1302, the separation of the anterior portions of the superior jaw section 1202 and inferior jaw section 1203 is not as great as when the separator 1207 is positioned in recesses 1301. Thus, this provides the surgeon or other practitioner with some varying heights at which to set the variable-opened-height controlled anchoring system in cage 1200. For example, when the separator 1207 is in recesses 1302, the height of the anterior portions of the superior jaw section 1202 and inferior jaw section 1203 can be 12 mm, and when the separator 1207 is in recesses 1301, the height of the anterior portions of the superior jaw section 1202 and inferior jaw section 1203 can be 16 mm.

While not shown in FIGS. 8A-8D, FIGS. 9A-9D, FIGS. 10A-10B, FIGS. 11A-11D, FIGS. 12A-12E, and FIGS. 13A-13F the cage embodiments can include holes through which other fasteners (such as screws) can then be inserted for further securing of the device. Such holes and fasteners are illustrated in FIGS. 3A-3C. Since cages 800 and 1200 can be anchored and secured prior to the insertion of these additional fasteners (using the anchoring systems), this provides additional freedom for the surgeon or other practitioner to properly insert and secure these fasteners because the cage is already being anchored.

Additional Cage Embodiments

Another embodiment of the present invention (cage 1400) is depicted in FIGS. 14A-14C. FIG. 14A is a superior/ inferior view of cage 1400 in the collapsed (non-expanded) form. FIG. 14B is a sagittal view of cage 1400 in a collapsed form (with the anterior portion of cage 1400 to the left in FIG. 14B). FIG. 14C is a sagittal view of cage 1400 in an expanded form (with the anterior portion of cage 1400 to the left in FIG. 14C). For better understanding, the cage portion (or spacer portion) 1404 of cage 1400 is shown transparently.

Cage 1400 has a cage portion 1404 that includes a top expandable portion 1401 and a bottom expandable portion 1402 that can be moved vertically moved, respectively, up and down relative to the superior/inferior surfaces of cage 1400 using lead screw 1403. Lead screw 1403 has an end that can be engaged with a positioning tool that can be used to hold on to the cage 1400 to properly position the cage 1400 between the opposing vertebrae.

When positioning the cage 1400, the positioning tool is capable of rotating the lead screw 1403 (either permanently or is locked in place to avoid rotation). Once the cage 1400 is in place, either the positioning tool is unlocked (and thus capable of rotating) or is unattached and a second tool (a rotational tool) is then attached to the lead screw. The lead screw is then rotated in a first direction (either clockwise or counterclockwise) which moves the lead screw 1403 forward (i.e., toward the front of the cage), which, in turn, causes the collar component 1405 to move the top expandable portion 1401 to move upward relative to cage portion 1404 and bottom expandable portion 1402 to move downward relative to cage portion 1404. Once the top expandable portion 1401 and the bottom expandable portion 1402 are expanded to the desired depths (upwards and downward), the cage is then anchored in place. The tool can then be unattached to the cage 1400 and, optionally, a locking mechanism can be utilized to maintain the lead screw in place (so that it cannot rotate), which will maintain the expandable portions 1401-1402 in the expanded position.

If desired, such as for removal of the cage or for repositioning of the cage, the rotational tool can be reattached and the lead screw can be rotated in a second direction, which will indirectly collapse expandable portions 1401-1402.

In this design, void spaces 1406 are within the cage 1400 that are not affected by the expansion of the expandable portions 1401-1402. It is in these void spaces 1406 that bone growth inducing substance can be placed.

Figure 15B:
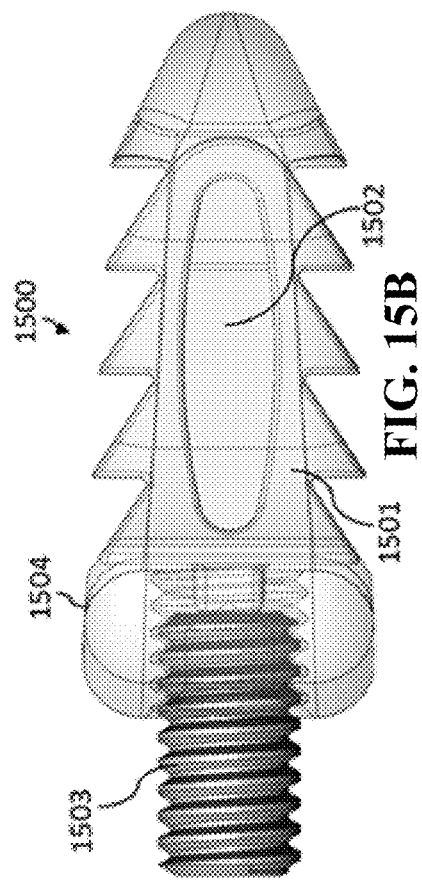
FIGS. 15A-15C depict different views of another embodiment of the present invention.
Figure 15C:
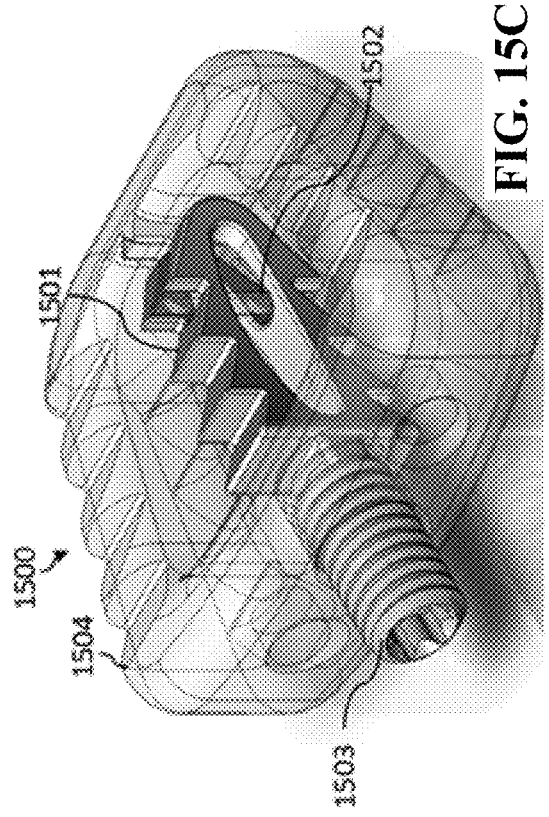
Figure 15A:
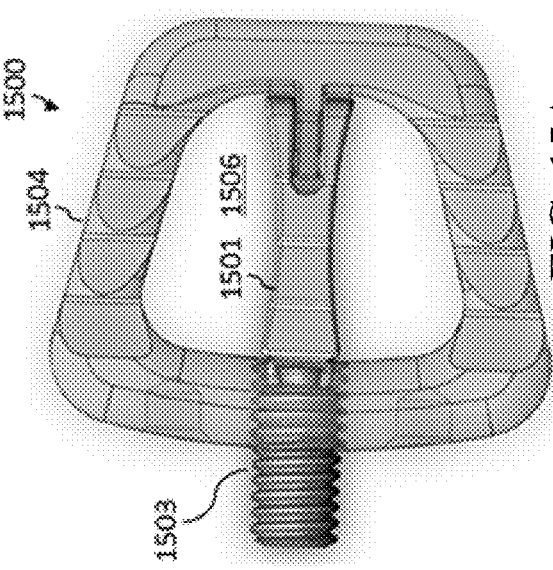

Another embodiment of the present invention is shown in FIGS. 15A-15C. FIG. 15A is a superior/inferior view of cage 1500 in the collapsed (non-expanded) form. FIG. 15B is a sagittal view of cage 1500 in a collapsed form (with the anterior portion of cage 1500 to the left in FIG. 15B), and (c) in FIG. 15C is a perspective view of cage 1500 in a collapsed form. For better understanding, the cage portion (or spacer portion) 1504 of cage 1500 is shown transparently.

As shown in FIGS. 15A-15C, the cage 1500 has an expandable flexible spring portion 1501 having an elliptical hole 1502. The expandable portion 1501 is capable of expanding vertically upwards and downwards relative to cage portion 1504. As the lead screw 1503 is rotated (by the rotational tool), this will move the lead screw 1503 to move forward (i.e., toward the front of the cage), which, in turn, causes the expandable portion 1501 to bow outward both upward and downward relative to cage portion 1504. Hence, this too anchors cage 1500 in a fashion similar to cage 1400 and can be utilized in a similar manner as described above. The cage 1500 likewise has a void spaces (void spaces 1506) in which bone growth inducing substance can be placed.

Figure 16B:
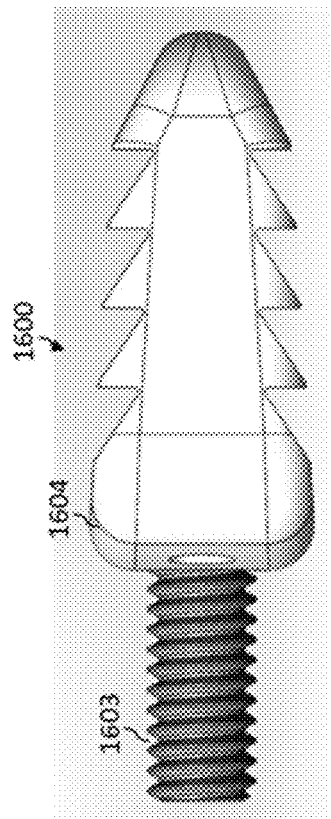
FIGS. 16A-16C depict different views of another embodiment of the present invention.
Figure 16C:
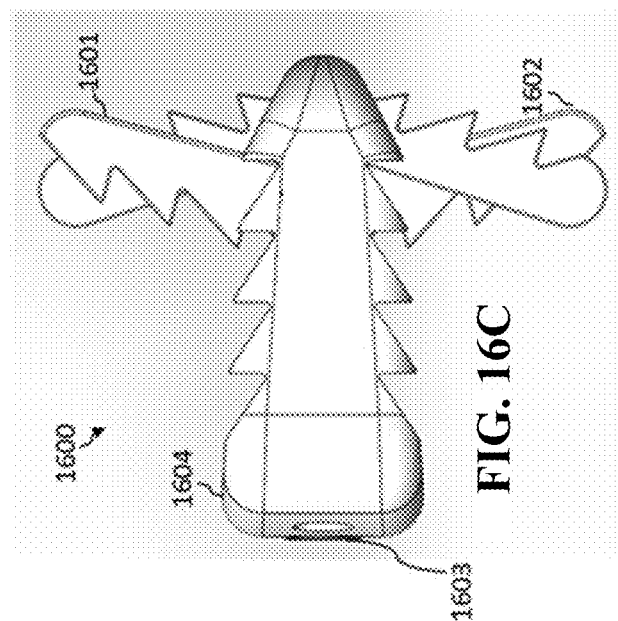
Figure 16A:
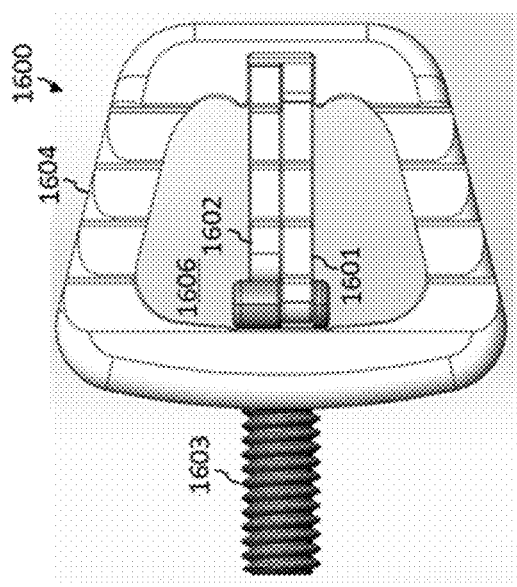

Another embodiment of the present invention is shown in FIGS. 16A-16C. FIG. 16A a superior/inferior view of cage 1600 in the collapsed (non-expanded) form. FIG. 16B is a sagittal view of cage 1600 in a collapsed form (with the anterior portion of cage 1600 to the left in FIG. 16B). FIG. 16C is a sagittal view of cage 1600 in an expanded form (with the anterior portion of cage 1600 to the left in FIG. 16C). For better understanding, the cage portion (or spacer portion) 1604 of cage 1600 is shown transparently.

As shown in FIGS. 16A-16C, the cage 1600 has a superior expandable linkage portion 1601 and an inferior expandable linkage portion 1602 that scissor/pivot vertically up and down, respectively (relative to cage portion 1604) as lead screw 1603 is rotated and moves forward relative to cage portion 1604. When these are expanded to the desired depths (vertically upwards and downward), the cage is then anchored in place. The expandable portion 1601 is capable of expanding vertically upwards and downwards relative to cage portion 1604. As the lead screw 1603 is rotated (by the rotational tool), this will move the lead screw 1603 to move forward (i.e., toward the front of the cage), which, in turn, causes the expandable portions 1601 and 1602 to pivot outward both upward and downward relative to cage portion 1604. Hence, these too anchor cage 1600 in a fashion similar to cages 1400 and 1500 and can be utilized in a similar manner as described above.

Cage 1600 likewise has a void spaces (void spaces 1606) in which bone growth inducing substance can be placed.

Another embodiment of the present invention is shown in FIGS. 17A-17D. FIG. 17A a superior/inferior view of cage 1700 in the collapsed (non-expanded) form. FIG. 17B, a sagittal view of cage 1700 in a collapsed form (with the anterior portion of cage 1700 to the left in FIG. 17B). FIG. 17C is a sagittal view of cage 1700 in a partially expanded form (with the anterior portion of cage 1700 to the left in FIG. 17C). FIG. 17D is a sagittal view of cage 1700 in a fully expanded form (with the anterior portion of cage 1700 to the left in FIG. 17D). For better understanding, the cage portion (or spacer portion) 1704 of cage 1700 is shown transparently.

As shown in FIGS. 17A-17D, the cage 1700 has a top expandable stabilizer portion 1701 and a bottom expandable stabilizer portion 1702 that can move vertically upward and downward relative to cage portion 1704 and thus can be utilized similar to cages 1400-1600 shown above. Lead screw 1703 has two portions, which generally will have different diameters. The first lead screw portion (portion 1707) is rotated and due to threading in cage portion 1704 will move forward relative to cage portion 1704. The second lead screw portion (portion 1708) engages with gear teeth 1710 on axle feature 1709. As portion 1708 moves forward relative to cage portion 1704, this will cause the gear teeth 1710 to mesh angularly about axle 1709, which will rotate top expandable stabilizer portion 1701 and a bottom expandable stabilizer portion 1702 upward and downward symmetrically, as shown in FIGS. 17C-17D. Hence, these too anchor cage 1700 in a fashion similar to cages 1400-1600 and can be utilized in a similar manner as described above.

Cage 1700 likewise has a void spaces (void spaces 1706) in which bone growth inducing substance can be placed.

Figure 18B:
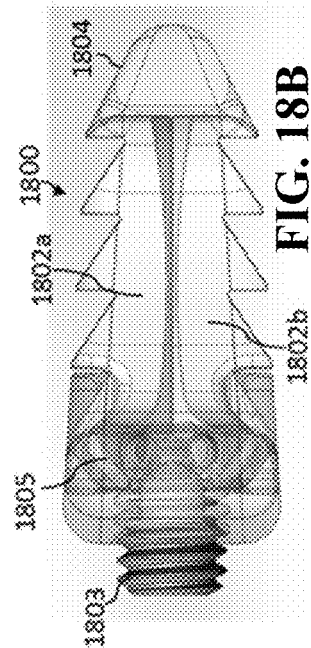
Figure 18D:
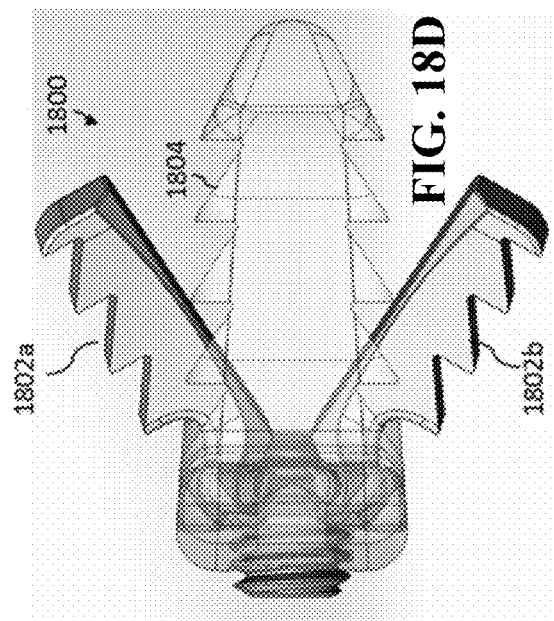
Figure 18A:
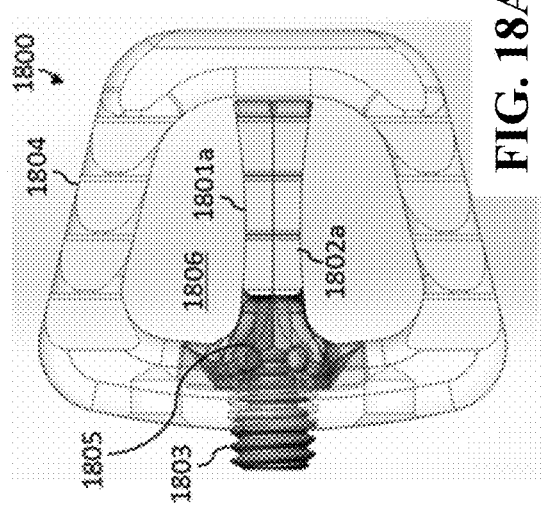
Figure 18C:
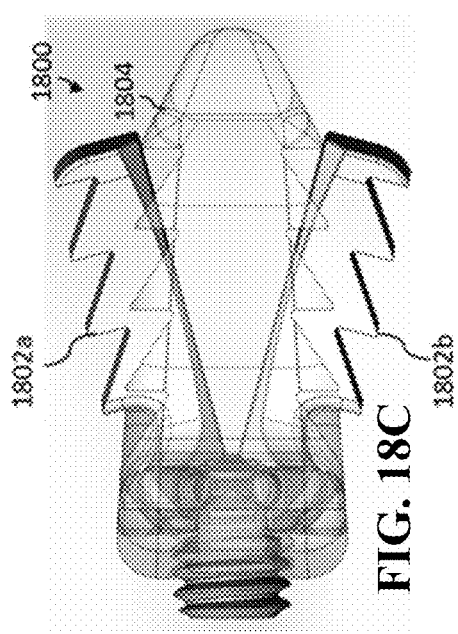
Figure 18H:
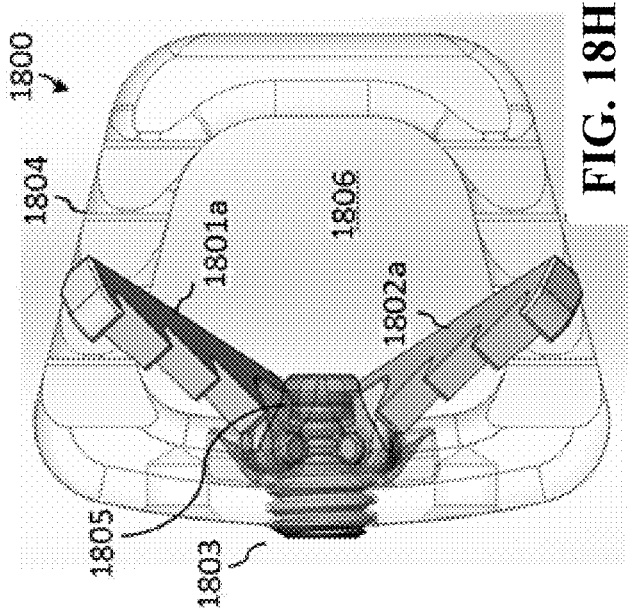
Figure 18G:
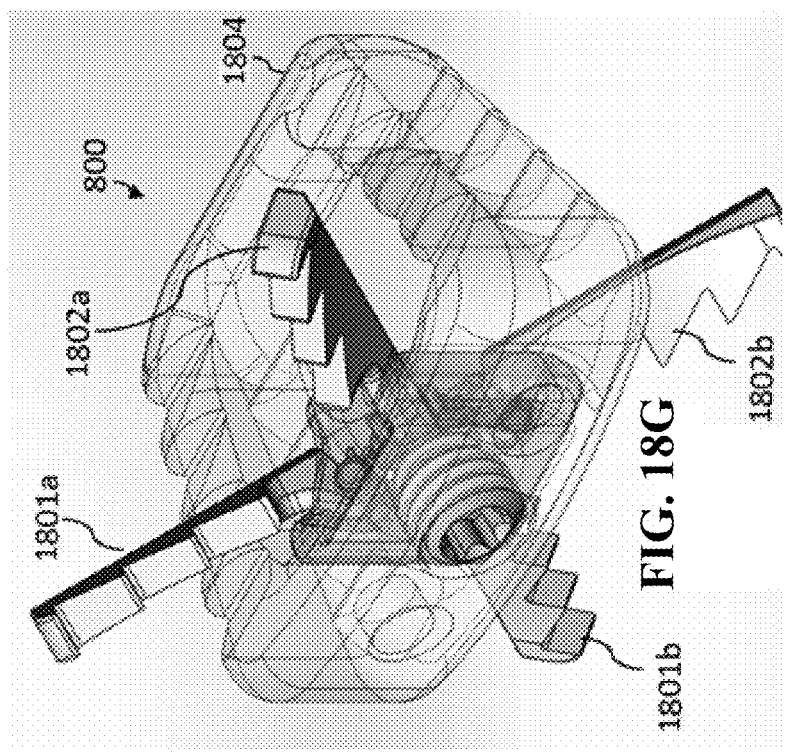

Another embodiment of the present invention is shown in FIGS. 18A-1811. FIG. 18A a superior/inferior view of cage 1800 in the collapsed (non-expanded) form. FIG. 18B is a sagittal view of cage 1800 in a collapsed form (with the anterior portion of cage 1800 to the left in FIG. 18B). FIG. 18C is a sagittal view of cage 1800 in a partially expanded form (with the anterior portion of cage 1800 to the left in FIG. 18C). FIG. 18D is a sagittal view of cage 1800 in a more partially expanded form (with the anterior portion of cage 1800 to the left in FIG. 18D). FIG. 18E is a sagittal view of cage 1800 in an even more partially expanded form (with the anterior portion of cage 1800 to the left in FIG. 18E). FIG. 18F is a sagittal view of cage 1800 in a fully expanded form (with the anterior portion of cage 1800 to the left in FIG. 18F). FIG. 18G is a perspective view of cage 1800 in a fully expanded form. FIG. 1811 is a superior/inferior view of cage 1800 in the even more partially expanded form (as shown in FIG. 18E). For better understanding, the cage portion (or spacer portion) 1804 of cage 1800 is shown transparently.

As shown in FIGS. 18A-1811, the cage 1800 has a top expandable stabilizer portions 1801a and 1801b and bottom expandable stabilizer portions 1802a and 1802b. Superior expandable stabilizer portions 1801a and 1801b can move vertically upward and laterally left and right, respectively, relative to cage portion 1804, while inferior expandable stabilizer portions 1802a and 1802b can move vertically downward and laterally left and right, respectively, relative to cage portion 1804. Such movement of superior expandable stabilizer portions 1801a and 1801b and inferior expandable stabilizer portions 1802a and 1802b occurs as lead screw 1803 is rotated and moved forward relative to cage portion 1804. When these are expanded to the desired depths (left upwards, right upwards, left downwards, and right downwards), the cage 1800 is then anchored in place. Hence, these too anchor cage 1800 in a fashion similar to cages 1400-1700 and can be utilized in a similar manner as described above.

Cage 1800 likewise has a void spaces (void spaces 1806) in which bone growth inducing substance can be placed Further Cage Embodiments with Anchoring Systems Further, cage 400 (shown in FIGS. 4A-4C and FIGS. 5A-5C), cage 600 (shown in FIGS. 6A-6D and FIGS. 7A-7D), cage 800 (shown in FIGS. 8A-8D, FIGS. 9A-9D, FIGS. 10A-10B, and FIGS. 11A-11D), cage 1200 (shown in FIGS. 12A-12E and FIGS. 13A-13F), cage 1400 (shown in FIGS. 14A-14C), cage 1500 (shown in FIGS. 15A-15C), cage 1600 (shown in FIGS. 6A-16C), cage 1700 (shown in FIGS. 17A-17D) and cage 1800 (shown in FIGS. 18A-18H) are depicted as non-expandable cages. In further alternative embodiments, the cage itself can be an expandable cage (vertically, laterally, or both). In the case that that the cage is expandable, the anchoring system needs to be such that it is independently moved from the closed position to an open positioned. Moreover, the anterior portions of superior anchoring section and inferior anchoring section generally must be at a greater difference than the height of the expandable cage (after expanded). In such way, the anchoring mechanism will be anchored even after the implant itself is expanded.

Uses of Cage Embodiments with Anchoring Systems

Figure 19:
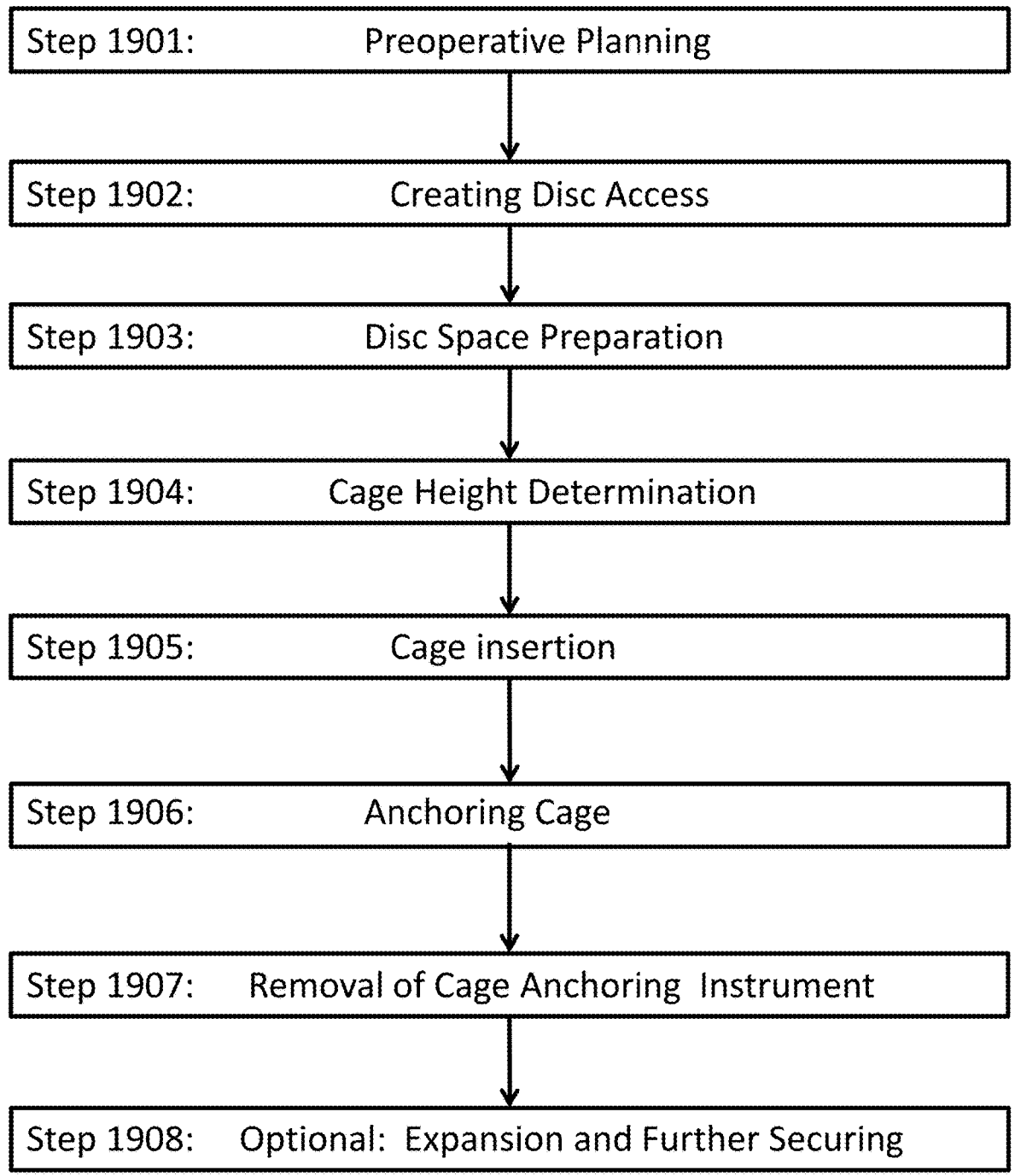
FIG. 19 is a flowchart of a surgical technique using the medical implants of the present invention.

A surgeon or other practitioner can use this medical implant in a method that includes the following steps:

FIG. 19 is a flowchart of a surgical technique using the medical implant that includes a cage having an anchoring system of the present invention (such as cages 400, 600, 800, 1200, 1400, 1500, 1600, 1700, and 1800).

In step 1901, the surgeon/practitioner performs preoperative planning. This includes determination of the appropriate height of the cage before the surgery. To achieve maximum segment height restoration, the cage should be selected having the largest possible height that can be safely inserted without disturbing the surrounding neural elements. Typically, the height is between 5 and 20 mm. Such preoperative planning should also take into account what the anchoring height should be. For example, if a single-opened-height controlled anchoring system is to be utilized, the surgeon/practitioner should select a cage that also includes the height the surgeon/practitioner desires. Further for example, if a variable-opened-height controlled anchoring system, the surgeon/practitioner should select a cage having a range of height that includes the height the surgeon/practitioner desires. (This preoperative planned heights of the cage and the anchoring system can be adjusted in step 1904 described below)

In step 1902, the surgeon/practitioner creates disc access. This, of course, depends on the surgical procedure being utilized by the surgeon/practitioner. I.e., the procedure an approach from the anterior, posterior, etc.). For the purposes of the description herein, the procedure will be oriented for an anterior approach. A person of skill in the art would understand how such procedure described below would be altered for other approaches. For instance in a typical anterior approach, the patient is placed in the prone position. From the midline anteriorly, the surgeon/practitioner would dissect the skin, subcutaneous tissues, and to expose (anteriorly) a portion of the spinal column. This exposed a disc space between adjacent vertebrae (or discs).

In step 1903, the surgeon/practitioner prepares the disc space. Using the appropriate instruments, the surgeon/practitioner removes the disc material. The surgeon/practitioner can decorticate the cartilaginous endplates from the surface of adjacent vertebral endplates until bleeding bone is obtained.

In step 1904, the surgeon/practitioner makes a height determination. Rasp trials may be used for further endplate preparation as well as to distract the vertebral space. This allows for the removal of small irregularities along the endplate better ensuring a smooth surface for cage insertion. Rasp or smooth trials can be used to determine the appropriate size of the cage to be inserted (and, if warranted, the surgeon/practitioner can modify which cage to utilize so that the appropriate heights of the cage and its anchoring system are proper). Trials also provide the surgeon with tactile feedback as it relates to the distraction of the vertebral space. The surgeon/practitioner can select a rasp or smooth trial that corresponds to the preoperative estimated height and the prepared endplates. The surgeon/practitioner can insert the rasp or smooth trial into the disc space until the desired height is achieved. The surgeon can confirm height and position visually and/or under fluoroscopy.

The surgeon/practitioner should then select a rasp or smooth trial that corresponds to the preoperative estimated height of the cage, as applicable. Trials that can be selected include parallel trials and lordotic trials. The surgeon/practitioner can apply gentle impaction to ensure that the trial fits tightly and accurately between the endplates. The surgeon/practitioner can then confirm height, depth, and position under fluoroscopy. Care should be taken to protect the nerve roots, dura, and spinal cord while placing rasp trials and/or smooth trials. (This is true also when inserting the implants, including the cage).

In step 1905, the surgeon/practitioner inserts the cage. Optionally, and typically before such insertion of the cage, the surgeon/practitioner can pack the grafting area of cage with bone graft (such as autologous bone graft) in the interior space of the cage. The surgeon/practitioner selects the cage that corresponds to the rasp trial or smooth trial size. The cage is inserted with the anchoring mechanism of the cage in the closed position. The surgeon/practitioner can attach the cage to an inserter tool and use this to insert the cage. (A tamp can be used to control the positing of the cage in the disc space). The surgeon/practitioner can insert the cage into the prepared intervertebral space. Gentle impaction on the multi-tool or inserter tool will assist in correct positioning.

Once properly positioned, in step 1906, the surgeon/practitioner can then secure the cage by rotating spindle or lead screw, as the case may be, so that the anchoring mechanism moves from the closed position to the opened position. Generally, this is done with a tool other than the multi-tool or inserter tool. However, such tools can be combined. This anchors and secures the cage by the opposing forces of the anterior portion of the superior anchoring section (superior jaw section) and the anterior portions of the inferior anchoring section (inferior jaw section) into the adjacent vertebral endplates. During this step the surgeon/practitioner can verify the proper placement and anchoring of the cage.

If the cage has multiple spindles or lead screws, each of the spindles/lead screws can be moved to cause the anchoring mechanism to be in the opened (anchored) position.

In step 1907, the instrument to move the one or more spindles/lead screws (as well as the multi-tool or inserting tool) is removed.

In steps 1908, which are optional steps, expansion of the cage and further securing can be performed by the surgeon/practitioner. For instance, if an expandable cage is utilized (which is not shown in the figures, but is well known in the art), the cage can be expanded laterally, vertically, or both, as the case may be. Moreover, the surgeon/practitioner can further secure the cage by using fasteners (such as screws). Because the cage is already secured and anchored, the cage stays in place during this further securement and anchoring, which facilitates the procedure for the surgeon/practitioner.

A medical procedure kit (or set) fully supports the surgical procedure to implant the cage using the medical implant fixation system can be supplied. Such kit can include one or more medical implant fixation devices (with medical implants, plates, and medical implant fixation instruments) and some or all of the following tools of a rasp trial, a smooth trial, another trial, inserter, and tamp.

The combination of tools and medical implant fixation systems can be pre-sterilized for ready use.

The disclosures of all patents, patent applications, and publications cited herein are hereby incorporated herein by reference in their entirety, to the extent that they provide exemplary, procedural, or other details supplementary to those set forth herein. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of approximately 1 to approximately 4.5 should be interpreted to include not only the explicitly recited limits of 1 to approximately 4.5, but also to include individual numerals such as 2, 3, 4, and sub-ranges such as 1 to 3, 2 to 4, etc. The same principle applies to ranges reciting only one numerical value, such as "less than approximately 4.5," which should be interpreted to include all of the above-recited values and ranges. Further, such an interpretation should apply regardless of the breadth of the range or the characteristic being described.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

What is claimed is:

1. A method comprising:
 (a) positioning a medical implant between a first vertebrae and a second vertebrae of a spinal column, wherein
  (i) the first vertebrae and the second vertebrae are adjacent, (ii) the medical implant comprises a medical implant body having a superior surface facing the first vertebrae and an inferior surface facing the second vertebrae,
(iii) the medical implant further comprises an anchoring mechanism, wherein the anchoring mechanism comprises
  (A) a superior anchoring section having an anterior portion of the superior anchoring section (superior-anchoring-section anterior-portion) and a posterior portion of the superior anchoring section (superior-anchoring-section posterior-portion),
  (B) an inferior anchoring section having an anterior portion of the inferior anchoring section (inferior-anchoring-section anterior-portion) and a posterior portion of the inferior anchoring section (inferior-anchoring-section posterior-portion), wherein
    (I) the superior-anchoring-section posterior-portion is pivotably connected to the inferior-anchoring-section posterior-portion at a pivot joint connected to and stationary relative to the medical implant body, and such that the superior-anchoring-section anterior-portion and the inferior-anchoring-section anterior-portion can move pivotably away from one another, and
    (II) the anchoring mechanism is in a closed position in which the superior-anchoring-section anterior-portion is in close proximity to the inferior-anchoring-section anterior-portion, and
  (C) at least one spindle or lead screw that is operable to move the anchoring mechanism from the closed position to at least one opened position,
(b) coupling a rotating tool to at least one of the at least one spindle or lead screw,
(c) using the rotating tool to rotate the at least one spindle or lead screw to move the anchoring mechanism from the closed position to one of the at least one opened position, wherein
  (i) the rotation of the at least one spindle or lead screw causes the superior-anchoring-section anterior-portion to move in a direction toward the first vertebrae and causes the inferior-anchoring-section anterior-portion to move in a direction toward the second vertebrae, such that the superior-anchoring-section anterior-portion and the inferior-anchoring-section anterior-portion anchor the medical implant between the first vertebrae and the second vertebrae, and
(d) removing the rotating tool from the at least one spindle or lead screw.

2. The method of claim 1, wherein
(a) the at least one spindle or lead screw is at least one spindle.

3. The method of claim 2, wherein:
(a) the medical implant body comprises at least one superior recess located at an anterior superior portion of the medical implant body and at least one inferior recess located at an anterior inferior portion of the medical implant body;
(b) the anchoring mechanism further comprises a compressor operatively connected to the superior anchoring section and the inferior anchoring section that provides a compressive force to compress the anchoring mechanism in the closed position;
(c) each of the at least one spindle has a separator, wherein
  (i) the at least one spindle is located between the superior-anchoring-section anterior-portion and the inferior-anchoring-section anterior-portion and at an anterior portion of the medical implant,
  (ii) the at least one spindle is rotatable so that the separator is operable to move between a first spindle position and a second spindle position,
  (iii) when the separator is in the first spindle position, the anchoring mechanism is in the closed position,
  (iv) when the separator is in the second spindle position, the anchoring mechanism is in the at least one opened position, and
  (v) when the separator is in the second spindle position, the separator is in contact with at least one of the at least one superior recess and at least one of the at least one inferior recess, which are operable to maintain the separator in the second spindle position which maintains the at least one spindle the second spindle position.

4. The method of claim 3, wherein the anchoring mechanism is a single-opened-height controlled anchoring system.

5. The method of claim 3, wherein the anchoring mechanism is a multiple-opened-height controlled anchoring system.

6. The method of claim 5, wherein:
(a) the medical implant body comprises at least one additional superior recess located at the anterior superior portion of the medical implant body and at least one additional inferior recess located at the anterior inferior portion of the medical implant body,
(b) the medical implant comprises a locking ring operable to lock the at least one spindle, wherein
  (i) the at least one spindle is rotatable so that the separator is operable to move between the first spindle position and a third spindle position,
  (ii) when the separator is in the third spindle position, the anchoring mechanism is in a second opened position that is different than the at least one opened position,
  (iii) when the separator is in the third spindle position, the separator is in contact with at least one of the at least one additional superior recess and at least one of the at least one additional inferior recess, and
  (v) the method further comprises utilizing the locking ring to lock the at least one spindle from rotating.

7. The method of claim 3, wherein the anchoring mechanism comprises at least two spindles.

8. The method of claim 1, wherein the at least one spindle or lead screw is at least one lead screw, and the anchoring mechanism is a variable-opened-height controlled anchoring system.

9. The method of claim 1, wherein the medical implant is a cage.

10. The med method of claim 9, wherein the cage is a lumbar cage.

11. The method of claim 9, wherein the cage is a cervical cage.

12. The method of claim 11, wherein the cervical cage comprises exactly one spindle or exactly one lead screw.

13. The method of claim 1, wherein the medical implant comprises a material selected from a group consisting of biocompatible radiolucent polymers, non-radiolucent metal alloys, carbon fibers, composites of carbon fibers and polymers, and combinations thereof.

14. The method of claim 1, wherein the anchoring mechanism comprises a material selected from a group consisting of metal alloys, ceramics, polymers, and composites thereof.

15. The method of claim 1, wherein the anchoring mechanism comprises a metal alloy or a carbon composite.

16. The method of claim 1, wherein the medical implant body is a non-expandable medical implant body.

17. The method of claim 1, wherein the medical implant body is an expandable medical implant body and the method further comprises expanding the medical implant body.

18. The method of claim 17, wherein the anchoring mechanism anchors the medical implant before expanding the expandable medical implant body.

19. The method of claim 1, further comprising a plurality of fastener window features through which, for each of the fastener window features in the plurality of window features, a fastener is passed through and used to anchor the medical implant.

20. The method of claim 19, wherein, for each of the fastener window features in the plurality of fastener window features, the fastener is selected from a group consisting of (a) fixed angle screws, (b) variable angle screws, (c) self-drilling screws, (d) self-tapping screws, and (e) combinations thereof.

* * * * *